(12) United States Patent
Kraus et al.

(10) Patent No.: US 7,911,598 B2
(45) Date of Patent: Mar. 22, 2011

(54) METHOD FOR CLEANING AN EUV LITHOGRAPHY DEVICE, METHOD FOR MEASURING THE RESIDUAL GAS ATMOSPHERE AND THE CONTAMINATION AND EUV LITHOGRAPHY DEVICE

(75) Inventors: Dieter Kraus, Oberkochen (DE); Dirk Heinrich Ehm, Lauchheim (DE); Thomas Stein, Oberkochen (DE); Harald Woelfle, Freiburg (DE); Stefan-Wolfgang Schmidt, Aalen (DE)

(73) Assignee: Carl Zeiss Smt AG, Oberkochen (DE)

( * ) Notice: Subject to any disclaimer, the term of this patent is extended or adjusted under 35 U.S.C. 154(b) by 10 days.

(21) Appl. No.: 12/555,620

(22) Filed: Sep. 8, 2009

(65) Prior Publication Data

US 2010/0034349 A1 Feb. 11, 2010

Related U.S. Application Data

(63) Continuation of application No. PCT/EP2008/001730, filed on Mar. 5, 2008.

(30) Foreign Application Priority Data

Mar. 7, 2007 (DE) .......................... 10 2007 011 480
Jun. 7, 2007 (DE) .......................... 10 2007 026 992
Jun. 7, 2007 (DE) .......................... 10 2007 026 993

(51) Int. Cl.
*G01N 21/73* (2006.01)
(52) U.S. Cl. .......................................... 356/72; 356/316
(58) Field of Classification Search .................... 356/72, 356/316
See application file for complete search history.

(56) References Cited

U.S. PATENT DOCUMENTS

| 5,669,979 | A | 9/1997 | Elliott et al. |
| 6,740,893 | B1 | 5/2004 | Tanabe |
| 2003/0046976 | A1 | 3/2003 | Hanazaki et al. |
| 2004/0007246 | A1 | 1/2004 | Chan et al. |
| 2006/0066824 | A1 | 3/2006 | Knappe et al. |

FOREIGN PATENT DOCUMENTS

DE 102 40 002 A1 3/2004

(Continued)

OTHER PUBLICATIONS

Cleaning of Contaminated XUV-optics at Bessy II, F. Eggenstein et al., Nuclear Instruments & Methods in Physics Research, Section A (467-468), pp. 325-328, Elsevier Science B.V., 2001.

*Primary Examiner* — F. L Evans
(74) *Attorney, Agent, or Firm* — Sughrue Mion, PLLC

(57) ABSTRACT

Components (30) in the interior of an EUV lithography device for extreme ultraviolet and soft X-ray wavelength range are cleaned by igniting a plasma, adjacent to the component (30) to be cleaned, using electrodes (29), wherein the electrodes (29) are adapted to the form of the component (30) to be cleaned. The residual gas atmosphere is measured spectroscopically on the basis of the plasma. An emission spectrum is preferably recorded in order to monitor the degree of cleaning. An optical fiber cable (31) with a coupling-in optical unit (32) is advantageously used for this purpose. Moreover, in order to monitor the contamination in the gas phase within the vacuum chambers during the operation of an EUV lithography device, it is proposed to provide modules configured to initiate a gas discharge and to detect radiation emitted on account of the gas discharge. The contamination in the gas phase can be deduced from the analysis of the measured spectrum.

30 Claims, 17 Drawing Sheets

FOREIGN PATENT DOCUMENTS

| | | |
|---|---|---|
| DE | 103 29 141 A1 | 2/2005 |
| DE | 10 2005 032 320 A1 | 1/2007 |
| EP | 0848434 A2 | 6/1998 |
| EP | 1517186 A1 | 3/2005 |
| GB | 2185573 A | 1/1986 |
| JP | 2004/186614 A | 7/2004 |
| JP | 2006/313847 A | 11/2006 |
| JP | 2007027237 A | 2/2007 |
| WO | 2006/020080 A2 | 2/2006 |

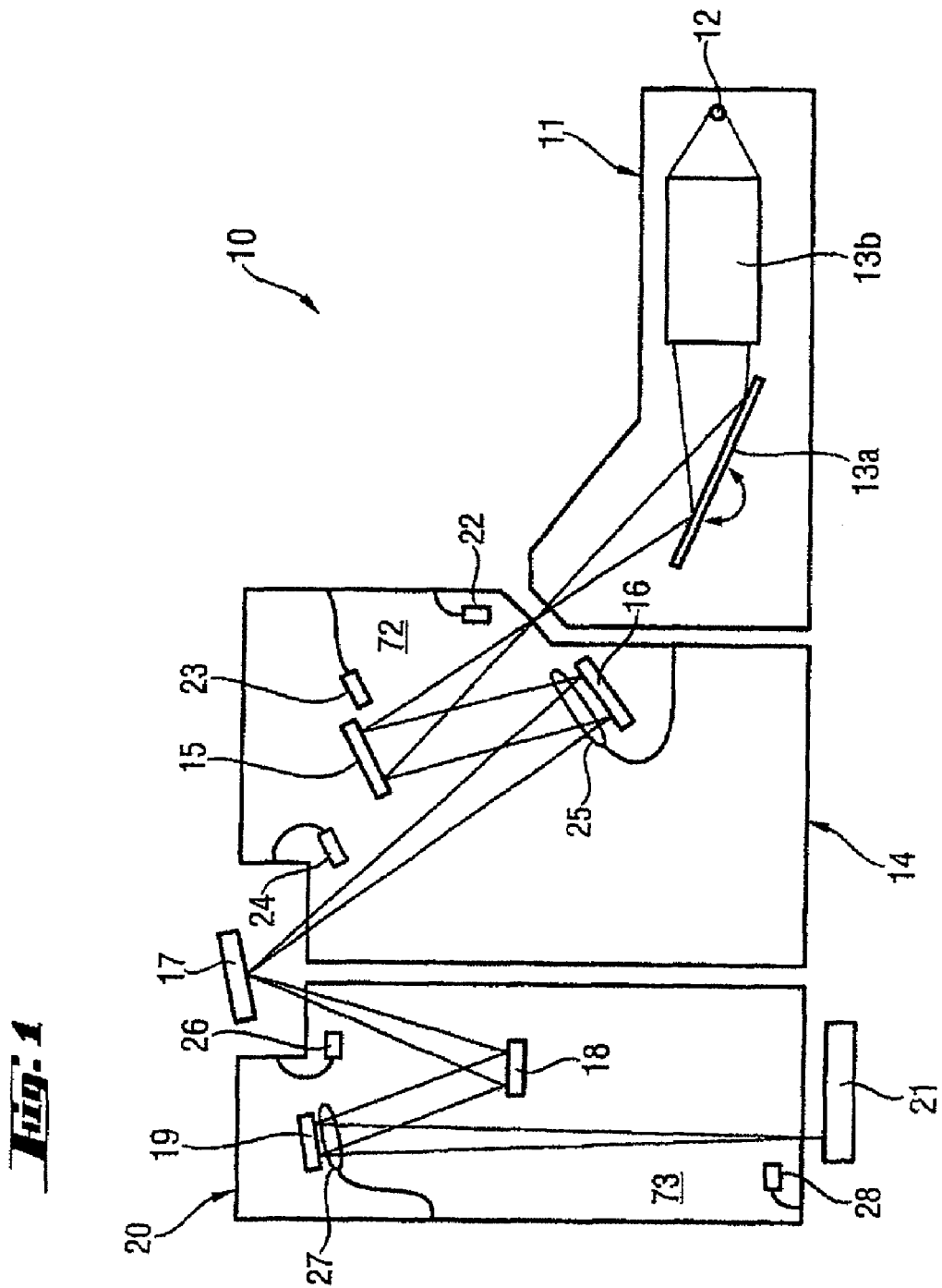

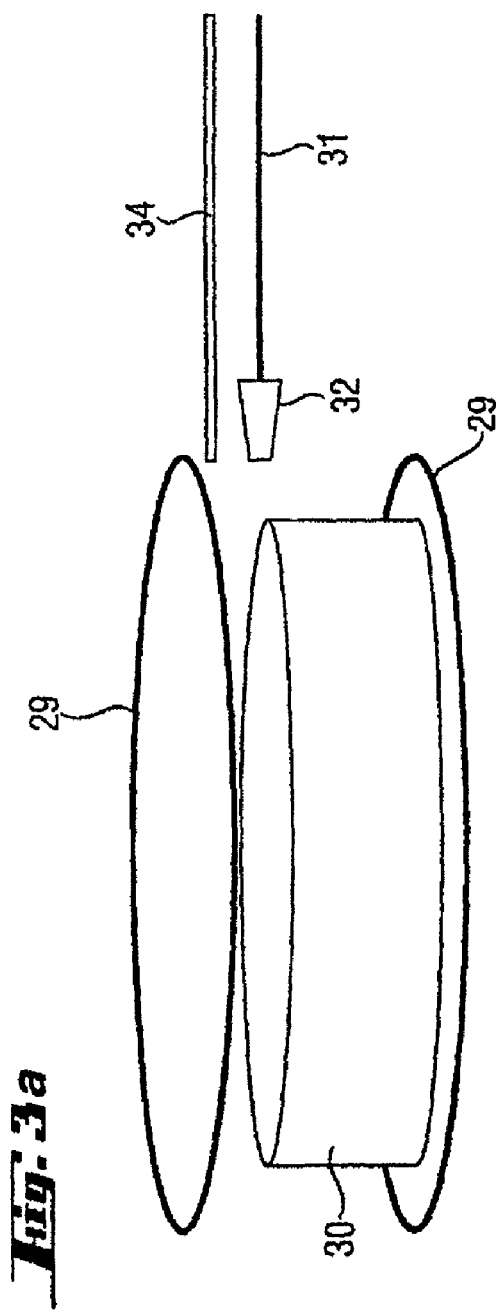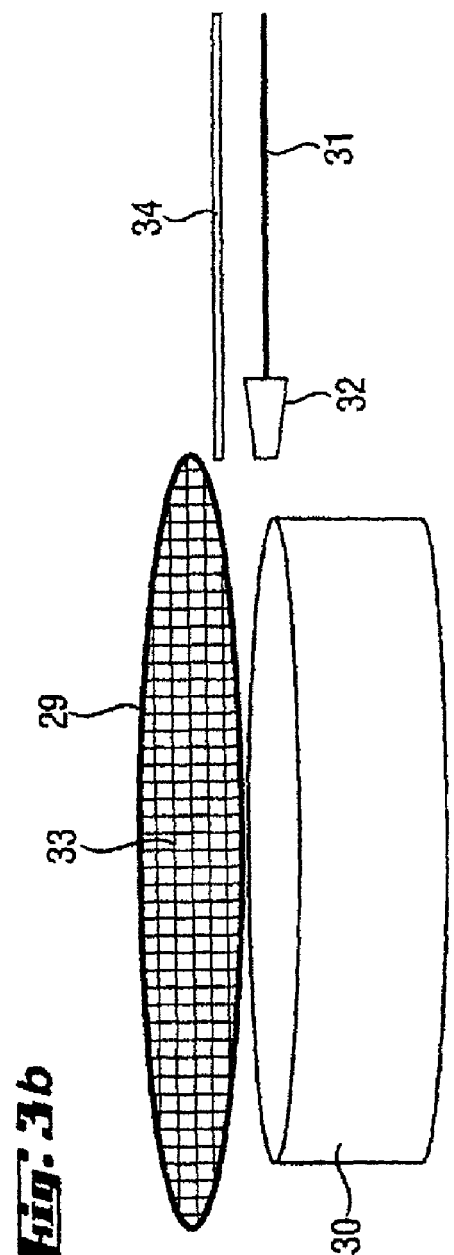

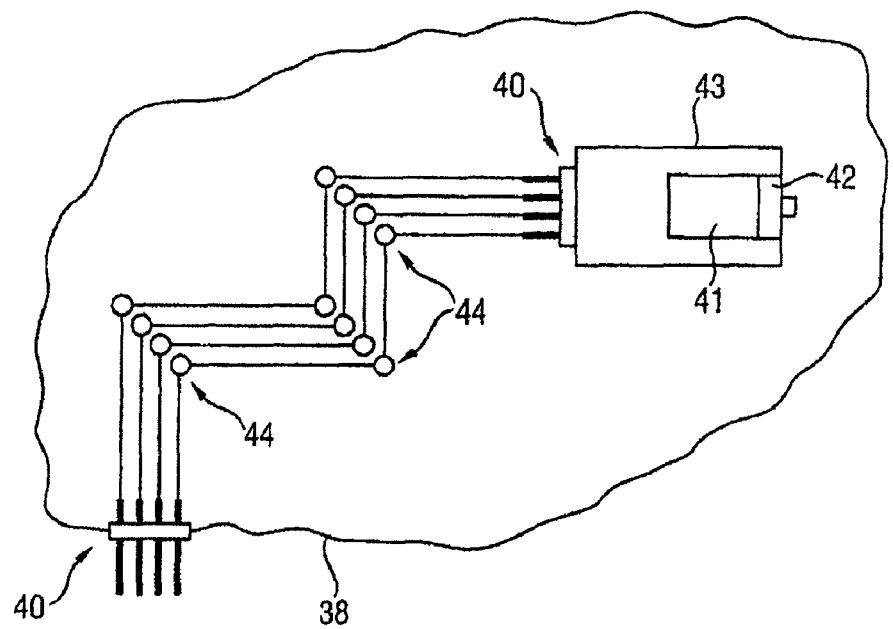
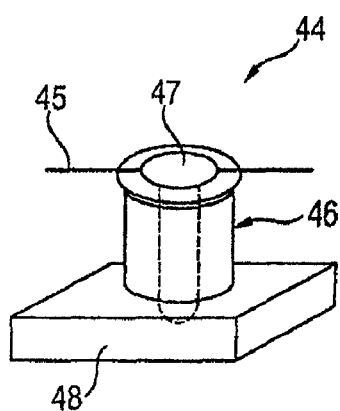
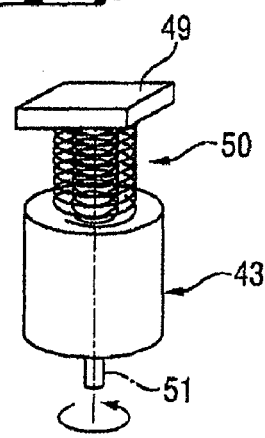

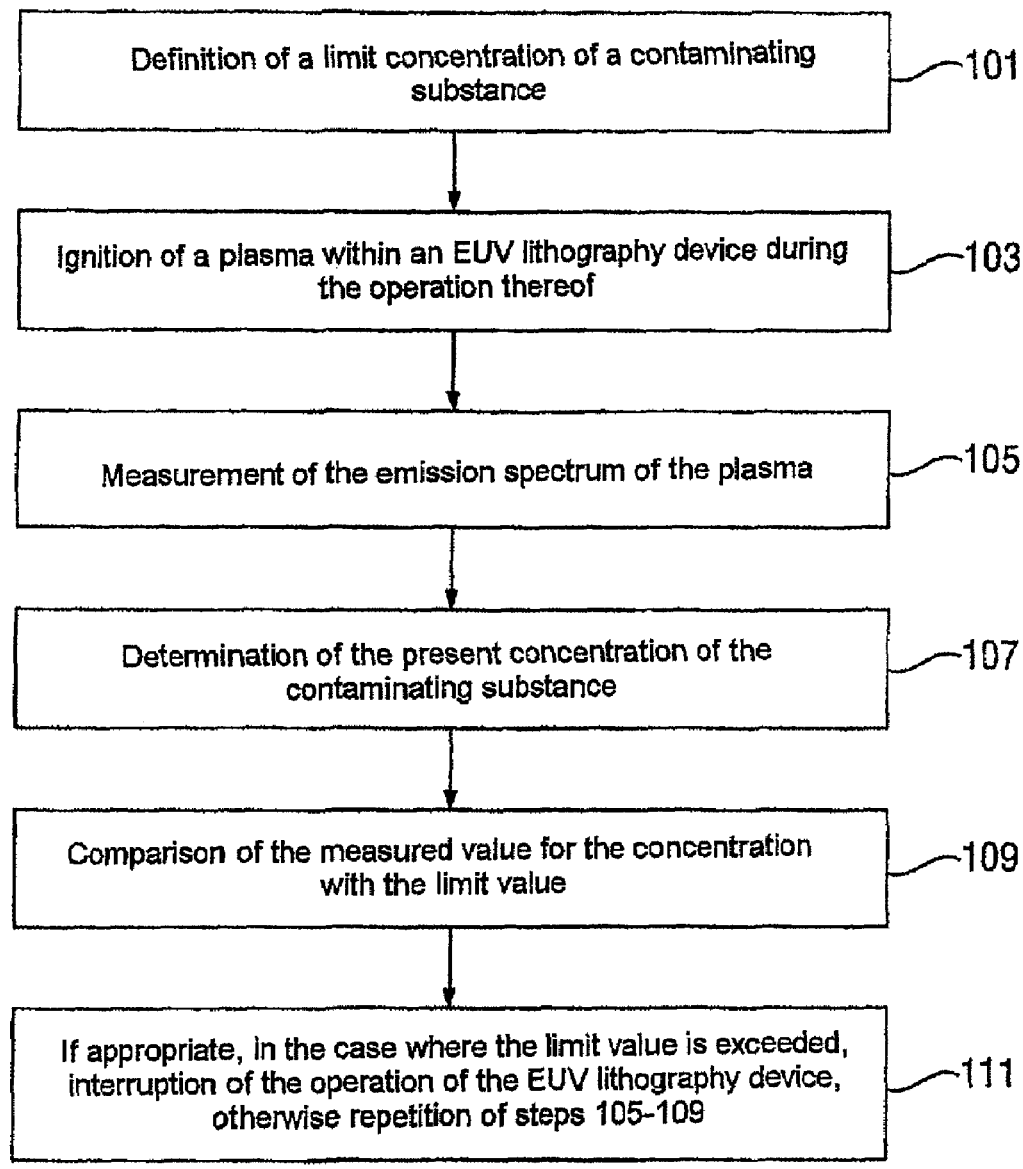

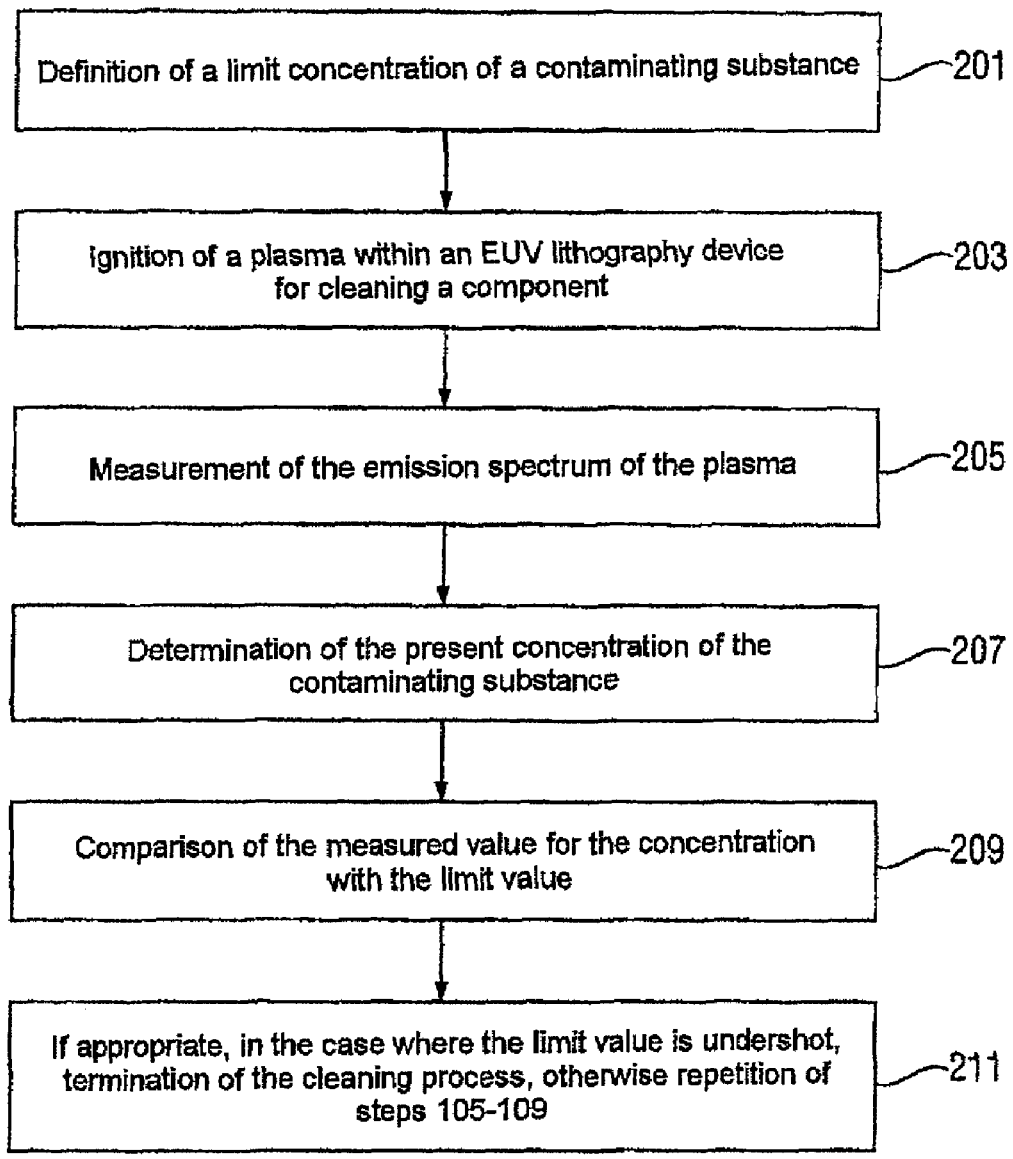

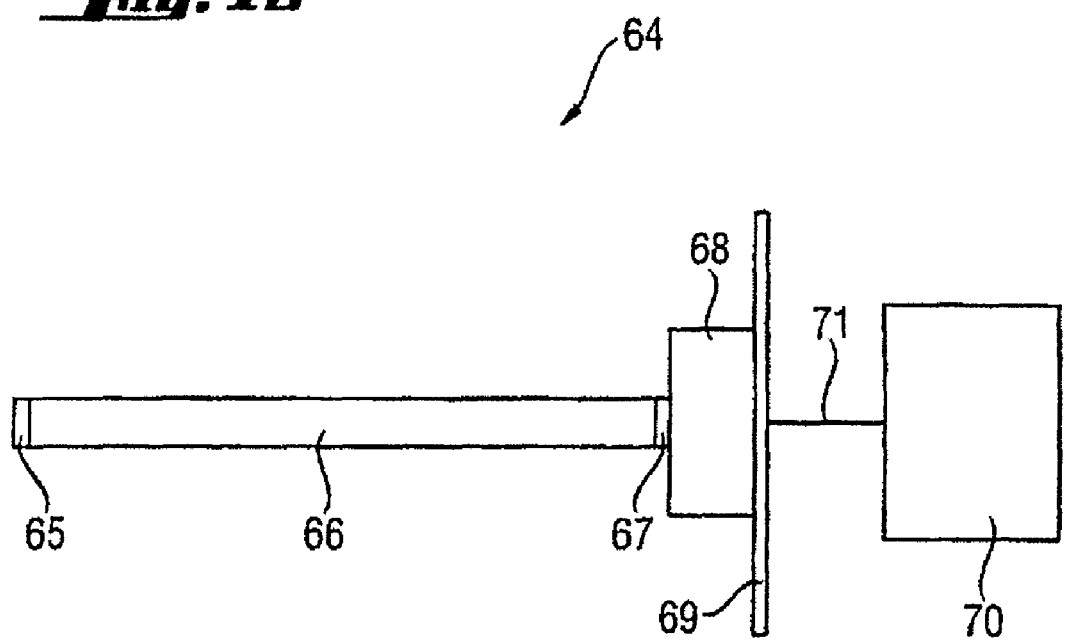

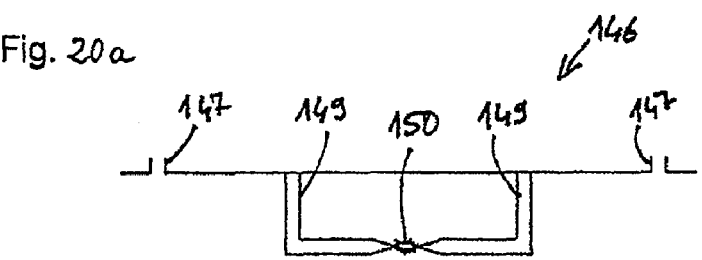
Fig. 20a
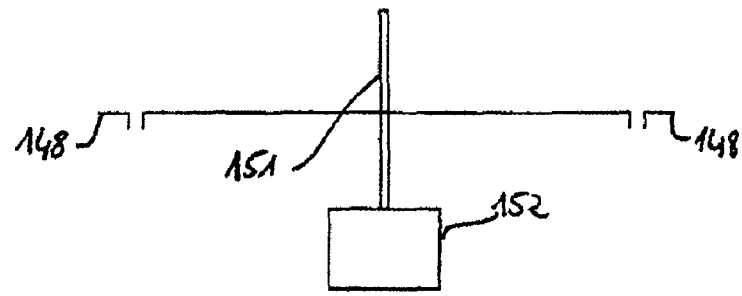
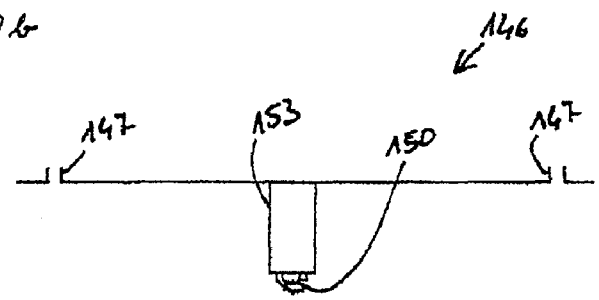
Fig. 20b
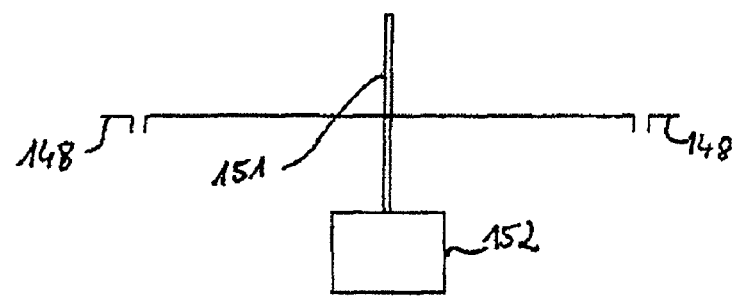
Fig. 21
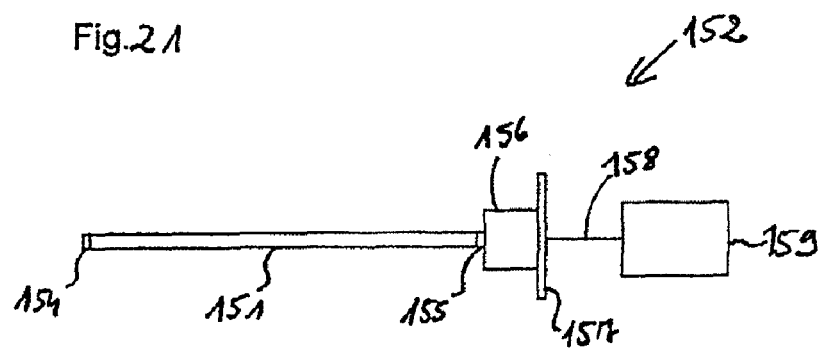

METHOD FOR CLEANING AN EUV LITHOGRAPHY DEVICE, METHOD FOR MEASURING THE RESIDUAL GAS ATMOSPHERE AND THE CONTAMINATION AND EUV LITHOGRAPHY DEVICE

This is a Continuation of International Application PCT/EP2008/001730, with an international filing date of Mar. 5, 2008, which was published under PCT Article 21(2) in German, and the complete disclosure of which, is incorporated into this application by reference.

FIELD OF THE INVENTION

The present invention relates to a method for cleaning components in the interior of an EUV lithography device for the extreme ultraviolet and soft X-ray wavelength range, and to a method for measuring the residual gas atmosphere in the interior of a vacuum chamber of an EUV lithography device. Moreover, the invention relates to a module for measuring the residual gas atmosphere. Furthermore, the invention relates to an EUV lithography device, and also to an illumination system and a projection system, in particular for an EUV lithography device.

The present invention also relates to a method for measuring contamination in EUV lithography devices. Furthermore, the invention relates to an EUV lithography device comprising a vacuum system having a vacuum chamber and a pump, and also to an illumination system and a projection system, in particular for an EUV lithography device, comprising a vacuum system having a vacuum chamber and a pump. However, the invention relates to a module for incorporation into a vacuum system of an EUV lithography device.

BACKGROUND AND RELATED ART

In EUV lithography devices, reflective optical elements for the extreme ultraviolet (EUV) and soft X-ray (SX) wavelength range (e.g. wavelengths of between approximately 5 nm and 20 nm) such as, for instance, photomasks or multilayer mirrors are used for the lithography of semiconductor components. Since EUV lithography devices generally have a plurality of reflective optical elements, the latter have to have a highest possible reflectivity in order to ensure a sufficiently high total reflectivity. The reflectivity and the lifetime of the reflective optical elements can be reduced by contamination of the optically utilized reflective area of the reflective optical elements, which arises on account of the short-wave irradiation together with residual gases in the operating atmosphere. Since a plurality of reflective optical elements are usually arranged one behind another in an EUV lithography device, even relatively small amounts of contamination on each individual reflective optical element effect the total reflectivity to a relatively great extent.

In order to ensure a sufficient lifetime in conjunction with good reflectivity, it is helpful to be able to monitor the composition of the residual gas atmosphere in order, in the event of a rise in the concentration of the gases that lead to contamination, to interrupt the operation of the EUV lithography device and if necessary to carry out cleaning in particular of the optical components. One possibility for in-situ cleaning consists in bombarding them with a jet of atomic hydrogen generated at a glow wire from molecular hydrogen flowing over the latter. On the one hand, relatively long-chain molecules on the surfaces to be cleaned are dissociated by the energy input; on the other hand, the atomic hydrogen reacts with the molecules to form volatile compounds that can be pumped away.

In vacuum systems for EUV lithography which have at least one vacuum chamber and a pump, the contamination in the gas phase should, moreover, always lie below specific limit values since otherwise, during the exposure process, the contamination from the gas phase interacts with the incident radiation in the EUV to soft X-ray wavelength range and is deposited onto the optically utilized areas of the reflective optical element.

SUMMARY OF THE INVENTION

It is an object of the present invention to make the operation of an EUV lithography device more manageable as regard to avoiding contamination.

This object is achieved by means of a method for measuring the residual gas atmosphere in the interior of a vacuum chamber of an EUV lithographic device for the extreme ultraviolet and soft X-ray wavelength range, in which a plasma is ignited in the interior of the vacuum chamber and a spectroscopic measurement is carried out on the plasma.

Since, in principle, all the residual gases present in the EUV lithography device are converted in the plasma, it is possible, in particular also during the operation of the EUV lithography device, by means of a spectroscopic measurement on the plasma, to determine the present composition of the residual gas atmosphere or to detect the presence of substances that are particularly critical for the contamination. It is likewise possible to detect the decrease thereof during cleaning.

Moreover, said object is achieved by means of a method for cleaning components in the interior of an EUV lithography device for the extreme ultraviolet and soft X-ray wavelength range, in which a plasma is ignited adjacent to a component having an area to be cleaned, wherein the plasma is ignited with the aid of an electrode whose form is adapted to the area of the component that is to be cleaned in such a way that the ignited plasma propagates over a region whose extent is restricted with a maximum deviation of approximately ±20% to the area to be cleaned.

Plasma cleaning with an adapted electrode form has the advantage firstly of being milder for the surfaces to be cleaned than conventional hydrogen cleaning, since contamination generated during the generation of the atomic hydrogen at the glow wire can be avoided and, in particular, the thermal load can be reduced. For the atomic hydrogen generated at the glow wire has a corresponding high temperature. The bombardment of the surface to be cleaned with the atomic hydrogen therefore results in a thermal input which, particularly if surfaces of optical components on the basis of multilayer systems are involved, can lead to a structural alteration of said multilayer systems, e.g. on account of diffusion processes at the layer boundary, which results in an irreversible reduction of reflectivity. Plasmas, by contrast, are ignited by coupling electromagnetic waves into the gas to be excited, such that the ions introduced into the plasma do not have a significantly higher temperature than the surface to be cleaned. Secondly, the method proposed here leads to more efficient cleaning since, by means of the electrode form, it is ensured that the plasma propagates substantially uniformly over substantially the entire surface to be cleaned.

The two methods are advantageously combined with one another to the effect that a spectroscopic measurement is carried out on the plasma used for cleaning a component. Since, during cleaning, the contaminating substances and/or their consequent products are also situated in the plasma, information about the present degree of cleaning is obtained near-instantaneously by means of the spectroscopic measurement, and without interrupting the cleaning, as would be necessary in the case of the conventional hydrogen cleaning.

Moreover, the object is achieved by means of a module for measuring the residual gas atmosphere in a vacuum chamber, in particular in a vacuum chamber of an EUV lithography device, which has means for igniting a plasma and means for measuring the emission or transmission of the plasma.

Furthermore, the object is achieved by means of an EUV lithography device for the extreme ultraviolet and soft X-ray wavelength range, which has in its interior an electrode for igniting the plasma, wherein the electrode is arranged adjacent to a delimited surface and is adapted in terms of its form to the contour of the surface in such a way that an ignited plasma propagates over a region whose extent is restricted with a maximum deviation of approximately ±20% to the delimited surface, and also by means of an illumination system and, respectively, a projection system, in particular for an EUV lithography device, which has in its interior an electrode for igniting the plasma, wherein the electrode is arranged adjacent to a delimited surface and is adapted in terms of its form to the contour of the surface in such a way that an ignited plasma propagates over a region whose extent is restricted with a maximum deviation of approximately ±20% to the delimited surface.

Finally, the object is achieved by means of an EUV lithography device for the extreme ultraviolet and soft X-ray wavelength range and, respectively, an illumination system, in particular for an EUV lithography device, and, respectively, a projection system, in particular for an EUV lithography device comprising a vacuum chamber and a module for measuring the residual gas atmosphere in a vacuum chamber, which has means for igniting a plasma and means for measuring the emission or transmission of the plasma.

The said object is also achieved by means of a method for measuring the contamination within a vacuum system of an EUV lithography device, in which within the vacuum system, by means of a gas discharge, electrons from matter present in the gas phase are excited to a higher energy level and the radiation which the excited electrons emit in the transition from the higher energy level to a lower energy level is detected. In particular, this demonstrates a possibility for measuring the contamination, in particular in EUV lithography devices, which can be carried out even during ongoing operation of the EUV lithography device. During a gas discharge, energy is transmitted to the atoms and molecules present in the gas phase in the region of the gas discharge, such that their electrons are excited to quantum-mechanically higher energy levels. After an extremely short time, the electrons revert to a lower state or their ground state and emit the energy difference in the form of photons. The energy or wavelength of the emitted photons is characteristic of the different atoms and molecules.

Since a gas discharge can be initiated well in a locally highly delimited space, it can be carried out without the operation of the EUV lithography device being appreciably influenced. Moreover, since the emission of the photons takes place directly upon initiation of the gas discharge and it is possible, by means of conventional spectroscopic measurement methods, to measure and evaluate the emission without delay, it is possible to obtain information about the contamination in the gas phase within the EUV lithography device very near-instantaneously, which information permits immediate reaction e.g. by feeding in other gases in order to reduce the risk of contamination by means of chemical reactions, or switching on additional pumping capacity, etc.

Furthermore, the object is achieved by means of an EUV lithography device comprising a vacuum system having a vacuum chamber and a pump, in which means for initiating a gas discharge and means for detecting the contamination within the vacuum system by means of the radiation emitted as a result of the gas discharge are arranged in the interior of the vacuum system, and also by means of an illumination system, in particular for an EUV lithography device, comprising a vacuum system having a vacuum chamber and a pump, in which means for initiating a gas discharge and means for detecting the contamination within the vacuum system by means of the radiation emitted as a result of the gas discharge are arranged in the interior of the vacuum system, and by means of a projection system, in particular for an EUV lithography device, comprising a vacuum system having a vacuum chamber and a pump, in which means for initiating a gas discharge and means for detecting the contamination within the vacuum system by means of the radiation emitted as a result of the gas discharge are arranged in the interior of the vacuum system.

The object is moreover achieved by means of a module for incorporation into a vacuum system of an EUV lithography device comprising means for initiating a gas discharge and means for detecting the contamination within the vacuum system by means of the radiation emitted as a result of the gas discharge. With the aid of the module it is possible to retrofit existing EUV lithography devices, illumination systems and projection systems in order to permit monitoring of the contamination even during operation.

Advantageous configurations are found in the dependent claims.

BRIEF DESCRIPTION OF THE FIGURES

The present invention will be explained in greater detail with reference to a preferred exemplary embodiment. For this purpose:

FIG. 1 schematically shows an embodiment of an EUV lithography device with an illumination system and a projection system;

FIGS. 3a-c schematically show a first and second variant of a plasma and measuring unit for emission measurements and a third variant for transmission measurements;

FIG. 6 schematically shows the fixing of a cable for current or voltage supply;

FIG. 7 shows the contact-connection of a vacuum-suitable drive;

FIG. 10 shows a flow chart concerning an embodiment of the method for measuring the residual gas atmosphere within an EUV lithography device;

FIG. 11 shows a flow chart concerning an embodiment of the method for cleaning a component within an EUV lithography device;

FIG. 18 shows a schematic illustration of a spectroscope;

FIG. 19 schematically shows an embodiment of an EUV lithography device with an illumination system and a projection system;

FIG. 20a schematically shows a first embodiment of a module;

FIG. 20b shows schematic a second embodiment of a module;

FIG. 21 shows schematic an arrangement for measuring the radiation emitted by the spark;

DETAILED DESCRIPTION OF THE INVENTION

Figure 2A:
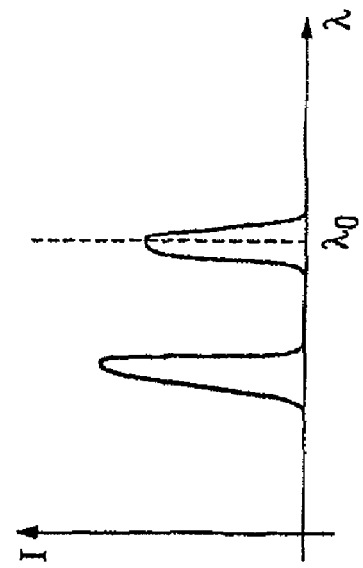
FIGS. 2a-d show basic schematic diagrams of different spectroscopic measurements.

FIG. 1 schematically illustrates an EUV lithography device 10. Essential components are the beam shaping system 11, the illumination system 14, the photomask 17 and the projection system 20.

By way of example, a plasma source or else a synchrotron can serve as radiation source 12. The emerging radiation in the wavelength range of approximately 5 nm to 20 nm is firstly concentrated in a collimator 13b. Moreover, the desired operating wavelength is filtered out with the aid of a monochromator 13a by varying the angle of incidence. In the stated wavelength range, the collimator 13b and the monochromator 13a are usually embodied as reflective optical elements. Collimators are often reflective optical elements embodied in shell-shaped fashion in order to achieve a focusing or collimating effect. The reflection of the radiation takes place at the concave area, in which case often a multilayer system is not used on the concave area for reflection purposes, since a widest possible wavelength range is intended to be reflected. The filtering out of a narrow wavelength band by reflection takes place at the monochromator, often with the aid of a grating structure or a multilayer system.

The operating beam conditioned with regard to wavelength and spatial distribution in the beam shaping system 11 is then introduced into the illumination system 14. In the example illustrated in FIG. 1, the illumination system 14 has two mirrors 15 and 16. The mirrors 15, 16 direct the beam onto the photomask 17, which has the structure that is intended to be imaged onto the wafer 21. The photomask 17 is likewise a reflective optical element for the EUV and SX wavelength range, which is exchanged depending on the production process. With the aid of the projection system 20, the beam reflected from the photomask 17 is projected onto the wafer 21 and the structure of the photomask is thereby imaged onto said wafer. In the example illustrated, the projection system 20 has two mirrors 18 and 19. It should be pointed out that the projection system 20 and the illumination system 14 can in each case have just one or else three, four, five or more mirrors. In most cases, the mirrors are situated in a vacuum in particular during lithography operation, for which reason the illumination system 14 and the projection system 20 of the EUV lithography device 10 have vacuum chambers 72 and 73, respectively.

The EUV or SX radiation itself, or the photoelectrons or secondary electrons generated by the irradiation, already leads to a small extent to the dissociation of hydrocarbon compounds, in particular also of low-volatility hydrocarbon compounds, into smaller hydrocarbon-containing molecules which can deposit as contamination on the optically utilized area of the reflective optical elements and thereby reduce the reflectivity thereof, particularly if a reaction with photons takes place.

In order to measure the occurrence and, if appropriate, also the concentration in particular of the hydrocarbon compounds, but also, if appropriate, of other contaminating substances in the residual gas atmosphere, modular plasma and measuring units 22-28 can be arranged at different location within the lithography device 10, preferably within the vacuum chambers 72, 73. Within the plasma and measuring units 22-28, a plasma is ignited by means of electrodes. All the present constituents of the residual gas atmosphere in this region of the EUV lithography device 10 are found in the plasma, such that accurate and concrete information about the present composition of the residual gas atmosphere within the EUV lithography device 10 can be obtained by means of spectroscopic examination of the plasma. The plasma can either serve for measuring the residual gas atmosphere during the operation of the EUV lithography devices 10, as in the case of the plasma and measuring units 22, 23, 24, or it can be used primarily for cleaning components 15, 16, 18, 19 within the EUV lithography device 10, as in the case of the plasma and measuring units 25, 27. In the case of parallel spectroscopic measurements on the plasma, the degree of cleaning that has already been effected can be deduced from the present composition of the residual gas atmosphere in the immediate vicinity of the component 15, 16, 18, 19 to be cleaned: during the plasma cleaning, the contaminated substances and/or their consequent products undergo transition to the gas phase and to the plasma. If their concentration starts to fall, this is an indication that less contamination is present on the surface of the component 15, 16, 18, 19 that has to be cleaned.

It should be pointed out that the plasma and measuring units can be designed in such a way that they are equally suitable for cleaning and for monitoring the residual gas atmosphere. In particular, the plasma stimulates the desorption of hydrocarbons in the residence region of the plasma, which de facto increases the detection sensitivity of contaminating substances in the residual gas atmosphere.

A wide variety of spectroscopic methods can be employed, such as e.g. transmission measurements. Emission spectroscopy is particularly preferred owing to the low outlay in respect of instrumentation in conjunction with high detection sensitivity in particular for hydrocarbons. The plasma contains all the chemical substances in a highly excited, ionized state in which they are excited to emit photons. In this case, each substance emits photons at one or more wavelengths characteristic thereof. Therefore, the composition of the plasma and hence the residual gas atmosphere can be measured directly from an emission spectrum.

Figure 2B:
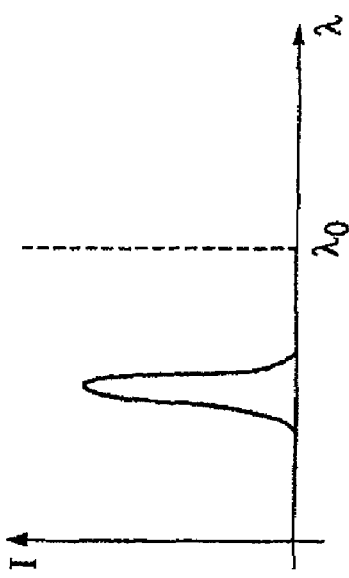

FIG. 2a illustrates in principle an emission spectrum for a pure plasma without appreciable residual gas. The intensity I is plotted as a function of the wavelength λ. In a pure plasma without residual gas, an emission occurs only at the characteristic wavelength of the plasma gas. If a contaminating substance from the residual gas were present in the plasma, there would additionally be an emission at the characteristic wavelength $\lambda_0$ of said contaminating substance, as is illustrated in principle in FIG. 2b. This information can be used to continuously monitor the residual gas atmosphere in a targeted manner with regard to specific contaminating substances over time.

Figure 2C:

Two preferred monitoring possibilities are illustrated as a basic schematic diagram in FIGS. 2c, d, in which specifically the concentration of the contaminating substance having the characteristic emission wavelength $\lambda_0$ is continuously monitored by means of the alteration of the emission intensity $I(\lambda_0)$ at said wavelength as a function of time t. FIG. 2c illustrates the case which involves monitoring, during the operation of the EUV lithography device, whether a sudden occurrence of the contaminating substance arises, e.g. as a result of a vacuum leak, or if the EUV or SX beam unintentionally alters its position and in the process impinges on a location at which the contaminating substance had deposited, which then undergoes transition to the gas phase as a result of the irradiation and thereby jeopardizes the optical components within the EUV lithography device. This is manifested in the emission measurement to the effect that firstly the intensity is negligibly low for a period of time, then rises sharply starting from a specific instant (FIG. 2c).

A limit value can be defined for the concentration or the partial pressure of the contaminating substance, said limit value corresponding to the intensity $I_0$ in FIG. 2c. As long as the measured intensity of the emission at the characteristic wavelength $\lambda_0$ varies below the limit intensity $I_0$, there is no risk of excessive contamination of the optical components of the EUV lithography device. As soon as the limit intensity $I_0$ is exceeded at a time $t_0$, there is the risk of contamination of the optical components that is so severe that the reflectivity decreases to an excessively great extent. The operation of the EUV lithography device should therefore be interrupted as quickly as possible before contamination occurs, in order that, by way of example, the interior of the EUV lithography device is additionally evacuated in order to remove the contaminating substance from the residual gas atmosphere.

Figure 2D:

FIG. 2d illustrates how the plasma cleaning process can be monitored with the aid of emission spectroscopy of the plasma. As a result of the interaction of the plasma with the contamination situated on the surface to be cleaned, the substance on which the contamination is based or its consequent products undergo transition to the plasma. Therefore, the intensity $I(\lambda_0)$ of the emission at the wavelength $\lambda_0$ that is characteristic of the contaminating chemical substance is initially very high. Gradually, however, in the plasma the entire contamination is converted into harmless compounds and the amount of contaminating chemical substance situated in the plasma decreases. The intensity $I(\lambda_0)$ of the emission at the wavelength $\lambda_0$ that is characteristic of the contaminating chemical substance also decreases to the same extent with time. In the present case, too, it is possible to define a limit value of the amount of contaminating chemical substance situated in the plasma, which limit value corresponds to a limit intensity $I_0$, and, in the case where said limit value is undershot, the surface to be cleaned can be regarded as sufficiently cleaned and the cleaning process can be ended at the time $t_0$.

It should be pointed out that FIGS. 2a-d are highly simplified for the purpose of better understanding of the functional principle. In the case of real gases and contaminating substances, emissions at a plurality of characteristic wavelengths with different relative intensities will be measured. Particularly during cleaning, depending on the contaminating substance, rather than the substance itself its consequent products after decomposition of the substance will be detected directly on the surface to be cleaned. However, the consequent products also emit photons at the characteristic wavelengths specific to them. Actually measured emission spectra will therefore be more complex than the basic schematic diagrams shown here. However, since emission spectroscopy as such is a measurement method that has been employed and researched for many decades, it is possible to have recourse to a very large and precise database of data particularly concerning the emission spectra of a multiplicity of chemical substances.

It should be pointed out that the explanations given here for emission spectroscopy essentially also apply to transmission spectroscopy.

In principle, not only the cleaning plasma but also the plasma for monitoring the residual gas atmosphere during the operation of the EUV lithography device can be ignited by means of any suitable gas desired. For monitoring the residual gas atmosphere during operation, inert gases are preferred in order to limit undesired interactions of the plasma with the EUV lithography device to a minimum. Since EUV lithography devices are often operated in a residual gas atmosphere having a high proportion of inert gas, preferably in a nitrogen, argon, krypton, helium or xenon atmosphere, if appropriate including in a hydrogen atmosphere or else a mixture of two or more of these gases, the partial pressure already present may already suffice to ignite a plasma. Particularly when there is a small electrode spacing, a plasma can already be ignited at partial pressures that are not overly high. This in turn has the advantage that the plasma is locally highly delimited and therefore only interacts minimally with the EUV lithography device and does not appreciably influence operation. In particular, it should be emphasized that the measurement of the residual gas atmosphere can be carried out by means of a spectroscopic measurement on the plasma without having to alter the operating conditions for the measurement. This is a major advantage with respect to conventional residual gas analyzer which are based on the principle of a mass spectrometer and can only be used at very low pressures, for which reason, for a hitherto conventional residual gas analysis, it is necessary firstly to improve the vacuum in the interior of the EUV lithography device. This is not necessary according to the method proposed here. For the case where the partial pressure of an ignitable plasma gas is too low, it is also possible to provide a gas feed which opens where the plasma is intended to be ignited. Inter alia, hydrogen, oxygen, nitrogen, noble gases, carbon monoxide, carbon dioxide, methane and higher homologs and mixtures of said gases are suitable as plasma gas. Electromagnetic waves from a frequency range of approximately $10^3$ Hz to $10^{11}$ Hz can be coupled in for igniting the plasma. Preferably, electromagnetic waves are chosen in the range of approximately $10^3$ Hz to $10^8$ Hz, particularly preferably in the range of approximately $10^5$ Hz to $10^7$ Hz for the high-frequency wavelength range, or of approximately $10^9$ Hz to $10^{10}$ Hz, particularly preferably of approximately $10^9$ Hz, for the microwave range. However, the frequency to be chosen depends to a very great extent on the gas used for ignition and also on the geometry of the electrode and the surfaces to be cleaned and possibly further adjoining surfaces and their material and should therefore best be determined from case to case. Moreover, it should be taken into consideration that in many countries the authorities respectively responsible have released only certain frequency bands for free use. When using microwaves, therefore, e.g. the frequencies 915 GHz and 2450 GHz are especially preferred.

Inert gases can also be used for a cleaning plasma. In the plasma they take up energy which they deliver to the contamination and in the process break up relatively long-chain molecules into volatile smaller molecules. However, gases which also react chemically with the contamination are also preferably used for the cleaning plasma. Hydrogen, having a reducing action, is particularly preferred. Oxygen can likewise be used, but it should be taken into consideration here that its oxidizing effect, which, in the case of excessively long application, can irreversibly damage the surface of optical components, particularly on the basis of a multilayer system. With the aid of the spectroscopic monitoring of the cleaning plasma as proposed here, by contrast, as described in connection with FIG. 2b, it is possible for a predetermined end point of the cleaning to be determined precisely and for the cleaning process to be ended in a timely manner before, for example in the case of multilayer systems, the terminating layer thereof below the contamination is reached, such that oxidizing gas can also be used without any problems as cleaning plasma gas, which would otherwise attack the terminating layer. However, in the case of other gases, too, determining the end point of the cleaning is highly advantageous in the context of process optimization.

As shown on the basis of the example of an EUV lithography device 10 illustrated in FIG. 1, the plasma and measuring units 22, 23, 24, 26, 28 for the measurement of the residual gas atmosphere during the operation of the EUV lithography device 10 can be arranged at a wide variety of locations within, in particular, the vacuum chamber 72 or 73 of the illumination system 14 or of the projection system 20. By way of example, such a unit can be arranged adjacent to a mirror, such as the plasma and measuring unit 23, for instance, which is arranged adjacent to the first mirror 15 in the beam path in the illumination system 14, said mirror being threatened the most by contamination owing to the highest radiation loading.

Another preferred position is the arrangement at the locations at which the EUV or SX beam enters into or emerges from the projection system 14 or the illumination system 20, as is the case for the plasma and measuring units 22, 24, 26, 28. These entrance or exit locations are embodied as dynamic gas locks, for example, in which a gas curtain is established by the outflowing of noble gases, said gas curtain being intended to prevent ingress of contamination. This is very important with regard to avoiding contamination since the wafer 21, in particular, is coated with photoresist, for example, which exhibits a high degree of outgassing, wherein contaminating substances emerge. In order to detect undesired ingress of contaminating substances as far as possible near-instantaneously, the plasma and measuring units 22, 24, 26, 28 are arranged in proximity to these critical locations.

The plasma and measuring units 25 and 27 are optimized for the cleaning of mirrors within the projection or illumination system. In particular, the electrode form is adapted to the contour of the surface to be cleaned. As a result, the cleaning plasma is situated as uniformly as possible directly on the surface to be cleaned, which ensures homogeneous cleaning. The homogeneous distribution of the plasma also makes it possible to employ fewer high-energy particles for cleaning than in the case of the hitherto conventional use of a directed particle beam, in which the particles have to have an energy high enough that they still exhibit a sufficient cleaning effect including at the locations remote from the particle beam. The means for the spectroscopic measurement of the plasma (not illustrated in detail here) of the plasma and measuring units 25, 27 are arranged in such a way that they do not project into the beam path during normal operation of the EUV lithography device 10. Optionally, for cleaning purposes, it is possible to use only the plasma without spectroscopic measurement or to monitor the cleaning process by means of spectroscopic measurements.

In further embodiments, the plasma and measuring units can also be embodied in movable or displaceable fashion. In particular the plasma and measuring units for cleaning in such a case are arranged such that they are situated completely outside the beam path during normal operation of the EUV lithography device and are only moved in the direction of the component if the respective component is intended to be cleaned. In this case, by way of example, a plasma and measuring unit can also be provided for the cleaning of a plurality of components situated in its movement radius. If appropriate, these movable plasma and measuring units can also be used, during normal operation of the EUV lithography device, if no cleaning is being carried out by them, to monitor the residual gas atmosphere.

FIGS. 3a,b,c schematically illustrate three preferred embodiments of electrodes optimized for the cleaning of a component of an EUV lithography device. In the examples illustrated, the substantially circular surface of an EUV multilayer mirror 30 is to be cleaned. In a manner adapted to the contour of the surface to be cleaned, the electrodes 29 are embodied as ring electrodes. Consequently, the plasma forms directly above and in a manner distributed comparatively uniformly over the entire surface to be cleaned. This leads to homogeneous cleaning of the surface and is a significant advance compared with cleaning by means of an atomic hydrogen jet generated at a glow wire. A further advantage over conventional hydrogen cleaning, moreover, is that, in contrast to the hydrogen atoms originating from a glow wire, the plasma does not transmit heat to the surface to be cleaned, such that thermally governed structural changes such as, for instance, diffusion processes at the layer boundaries within the multilayer system, which would result in an irreversible loss of reflectivity, are not caused. For the plasma is ignited by high-frequency electromagnetic or microwave radiation, for example, being coupled into the plasma gas via the electrodes 29.

A plasma is ignited adjacent to a component having an area to be cleaned, wherein the plasma is ignited with the aid of an electrode whose form is adapted to the area of the component that is to be cleaned in such a way that the ignited plasma propagates over a region whose extent is restricted with a maximum deviation of approximately ±20% to the area to be cleaned.

Preferably, the density of the plasma is adapted to the degree of contamination. In particular, the density distribution of the plasma is set in such a way that a higher removal is effected in surface regions of the component to be cleaned having a higher degree of contamination than in surface regions having a lower degree of contamination.

Advantageously, a specific energy distribution of the plasma is formed on the area to be cleaned. In particular, the energy distribution of the plasma is set in such a way that a higher removal is effected in surface regions of the component to be cleaned having a higher degree of contamination than in surface regions having a lower degree of contamination.

Figure 9:
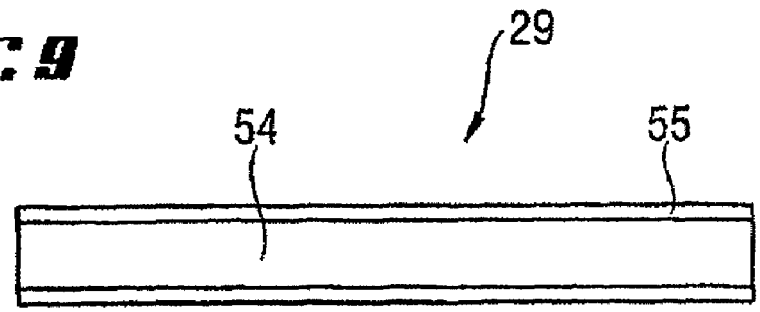
FIG. 9 schematically shows the construction of an electrode.

The electrode material used can be any desired metals or metal alloys having a high melting point, such as tungsten, for example. In order to minimize the risk of contamination on account of electrode material sputtered by the plasma, the actual electrode 54 is preferably sheathed with a sputtering-resistant material 55, as is illustrated schematically in FIG. 9. By way of example, fused silica is particularly preferred, which is not only sputtering-resistant but also has a high transparency to, for example, high-frequency electromagnetic or microwave radiation that is intended to be used to ignite the plasma. The avoidance of sputtering of the electrode material is a further strength of the plasma cleaning proposed here by comparison with the conventional cleaning by means of an atomic hydrogen jet induced by a glow wire. For in the latter case it has not been possible hitherto to sufficiently prevent material of the glow wire from being sputtered and depositing on the surface to be cleaned.

The arrangements in FIG. 3a and FIG. 3b differ to the effect that two electrodes 29 are employed in FIG. 3a, while in FIG. 3b the mirror 30 is grounded and itself acts as a counter electrode with respect to the electrode 29. In order to locally delimit the plasma effectively, in order e.g. that it does not interact with other components within the EUV lithography device in an undesired manner, in the arrangement from FIG. 3b the electrode 29 is provided with a wide-mesh metallic net 33, which acts as a shield. The net 33 is preferably composed of customary electrode material. Particularly preferably, the net 33 as sputtering protection is likewise coated with fused silica, for example. Although the net 33, given appropriate dimensioning, has no adverse influence on the exposure or projection process, arrangements having a net 33 are preferably embodied in movable fashion in order to be moved out of the beam path after the cleaning process, in order to minimize possible transmission losses of the EUV or SX radiation.

Figure 3C:
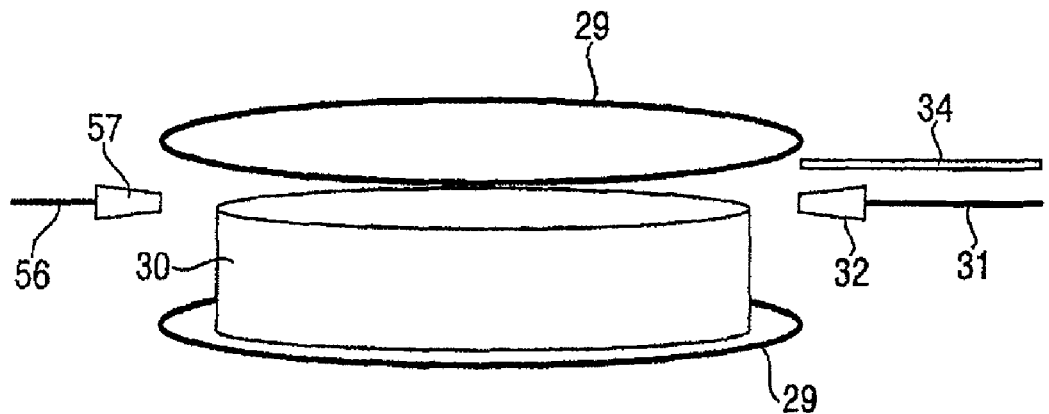

All the arrangements from FIGS. 3a,b,c have a gas feed 34 that opens where the plasma is intended to be ignited, in order to make the plasma gas available. In order to analyze the plasma with regard to its composition and thus with regard to the degree of cleaning, means 31, 32 for carrying out spectroscopic measurements are provided. In the example illustrated here, the emission of the plasma is measured with the aid of an optical fiber 31, which transmits the emitted photons to a spectrometer outside the EUV lithography device. For this purpose, the emitted photons are coupled into the fiber 31 via a suitable optical element 32. Optical fibers, in particular glass fibers, have the advantage that they do not exhibit outgassing in the vacuum even upon irradiation with EUV or soft X-ray radiation and, moreover, have a minimal space requirement, such that the operation of the EUV lithography device is not impaired. All remaining components which would be necessary for the measurement but have a certain space requirement and are possibly not vacuum-suitable can be combined for example in an externally located spectrometer 64. For transmission measurements, as illustrated in FIG. 3c, a light source situated opposite is additionally provided, in which case an optical fiber 56 and an optical element 57 for coupling out the photons from the fiber 56 are likewise employed in a space-saving manner in order to transmit light from an external light source to the plasma.

One example of a suitable embodiment of the spectrometer 64 is illustrated schematically in FIG. 18. For coupling the emitted photons into the optical fiber 66, an optical element in the form of a coupling-in unit 65 is provided at one end of said fiber. For coupling out the photons from the optical fiber 66, a corresponding coupling-out unit 67 is provided at the other end of said fiber. From there the photons enter into an energy-dispersive analyzer, for example a grating monochromator 68, in order to record an energy-resolved spectrum of the emitted photons. For this purpose, the photons are diffracted by a different angle at the grating monochromator 68 depending on their energy or wavelength, such that they impinge at different locations on a two-dimensional detector, here a CCD detector 69. Upon impinging on the detector 69, the photons are converted into electric current which is proportional to the number of photons in the respective energy range and is read out separately for each energy range. In the present example, an oscilloscope 70 is used for this purpose, said oscilloscope being connected to the CCD detector 69 via a read-out cable 71. In simpler cases, it is also possible for example to dispense with the energy resolution, by means of the photons being measured directly or with the aid of an optical fiber by a photodetector. Fluctuations in the quantity of detected photons or corresponding fluctuations in the photocurrent generated permit conclusions to be drawn about the increase or decrease in the quantity of contaminating substances in the immediate vicinity of the plasma.

Figure 12A:
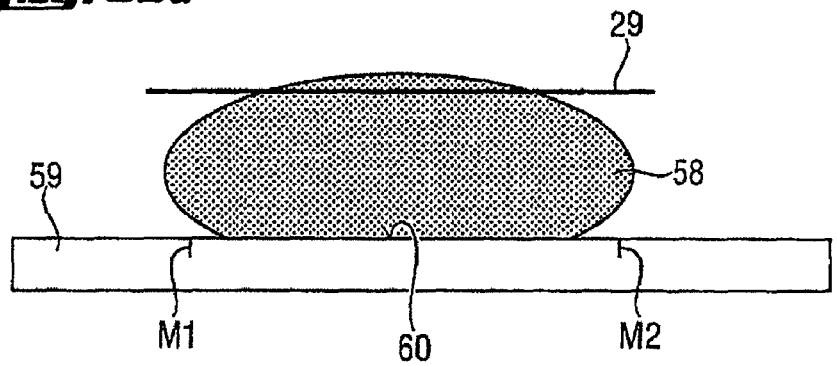
FIGS. 12a, b show schematic illustrations of plasmas having different densities.

FIGS. 12a,b, schematically illustrate two electrode arrangements which lead to plasmas having different plasma densities. An electrode 29 is in each case arranged above the components 59 to be cleaned, wherein the component 59 acts as a counter electrode. The electrode 29 is arranged above an area 60 to be cleaned, which is delimited by the markings M1, M2 in FIGS. 12a,b. The electrode 29 is adapted in terms of its form to the area 60 of the component 59 that is to be cleaned in such a way that the plasma 58 ignited by microwave irradiation, for example, is restricted by ±20%, preferably ±10%, particularly preferably ±5, to the area to be cleaned. The intended aim is that in terms of its extent at the level of the area 60 to be cleaned the plasma is approximately congruent with the area 60 to be cleaned, in order to ensure cleaning that is as efficient as possible. Preferably, the area 60 to be cleaned corresponds to the area of a reflective optical element, e.g. of a mirror, which is optically utilized during operation, for example is illuminated with an operating radiation in the case of a mirror. Contaminations are particularly disturbing in this region.

Figure 12B:
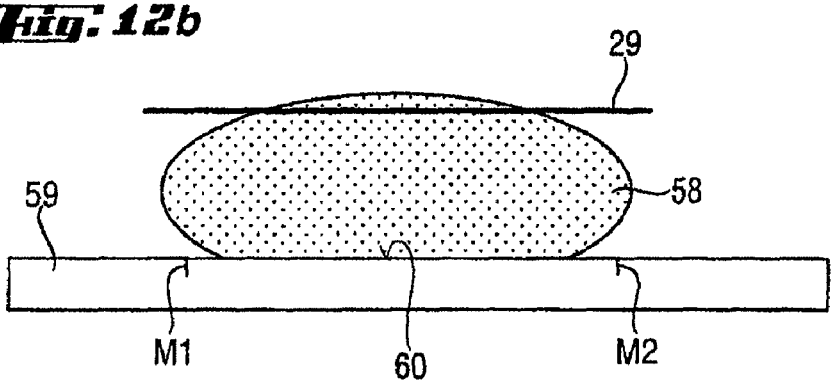

The plasma 58 from FIG. 12a has a higher plasma density than the plasma 58 from FIG. 12b, which is symbolized by the dotting having different densities. The plasma density is influenced, inter alia, by the frequency used of the electromagnetic wave that is coupled in, by the form of the electrode 29 and by the electrode spacing, that is to say the spacing between electrode 29 and the component 59 in the example shown here. What is essentially of importance is that a standing wave forms between the electrodes, such that a high power density is made available locally, such that a plasma forms. The material of the component 59 and/or of the contamination to be removed should also be taken into consideration to a certain extent in this case. An important parameter, particularly in the case of a fixed geometrical configuration, is the power of the electromagnetic wave coupled in. A higher power radiated in leads to a higher plasma density.

Figure 13:
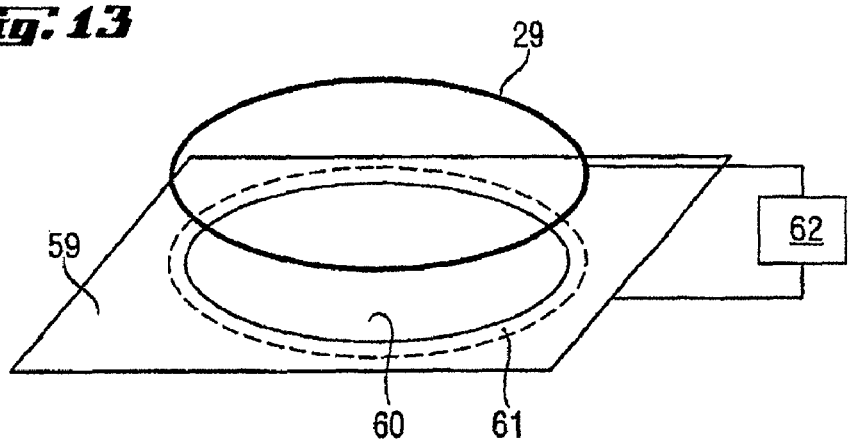
FIG. 13 shows a schematic illustration of an electrode arrangement.

FIG. 13 correspondingly illustrates an electrode arrangement having means for setting the coupled-in power in the form of the regulator 62. With the aid of the regulator 62, the plasma density can be adapted, by means of the power coupled in, to the distribution and density of the contamination to be removed. The higher the plasma density, the higher the cleaning effect. What can be achieved by using two-dimensional electrodes, such as a ring electrode 29, for instance, is that the electromagnetic waves radiated in, such as microwaves, for instance, do not form a uniform wavefront, but rather have a different power distribution over the area to be cleaned. This can be utilized for the removal of contamination that grows in a foreseeably inhomogeneous manner. In the dimensioning of electrodes with adjustable power, it should be taken into consideration that the plasma that arises can have a larger extent at higher density. In the example illustrated in FIG. 13, the electrode size is chosen such that the area 61 which is defined by the electrode 29, and which is indicated by the dashed line, is somewhat larger than the area 60 to be cleaned, in order to compensate for possible fluctuations in the plasma extent, in order that the entire area 61 to be cleaned is covered by the plasma as far as possible in many cases. The area 61 defined by the electrode 29 should cover the area 60 to be cleaned to the extent of 70-150%, preferably 90-120%, particularly preferably 95-110%, especially preferably 98-105%.

Figure 14:
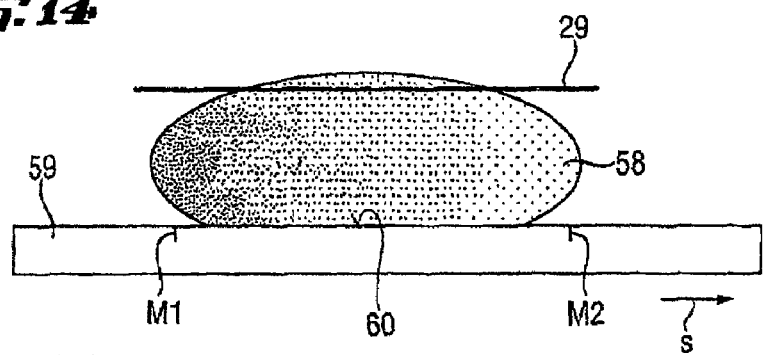
FIG. 14 shows a schematic illustration of a plasma having a specific energy distribution.
Figure 15:
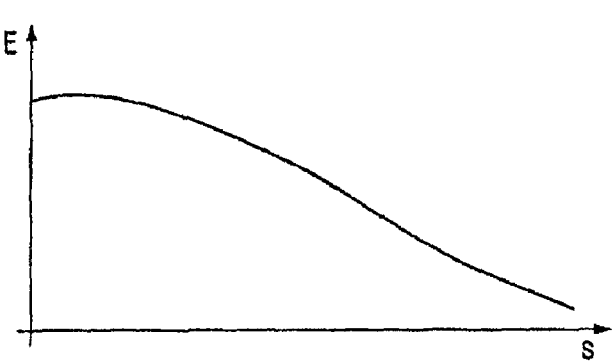
FIG. 15 shows a schematic illustration of the energy distribution of the plasma from FIG. 14.

FIG. 14 illustrates a plasma 58 having a decreasing energy distribution over the distance s. This is symbolized by the color profile becoming lighter. A corresponding graph of the energy E versus the distance s is illustrated in FIG. 15. The plasma energy distribution can be determined e.g. by means of the energy distribution of the electrons and/or ions present in the plasma. The energy distribution of the electrons and ions correlates to the effect that the profile is substantially identical, but differs owing to the different masses of the absolute energy magnitude. To a first approximation, a high plasma density and likewise a high power density of the electromagnetic radiation coupled in lead to a high energy at a specific location. The energy distribution correlates closely with the cleaning effect of the plasma at the specific location. For the more energy the electrons and ions have in the plasma, the more energy they can pass on to the contamination in order to dissociate the latter and, if appropriate, to react with the contamination or the dissociation products. The aim is for as much contamination as possible to be converted into volatile compounds that can be pumped away.

Figure 16:
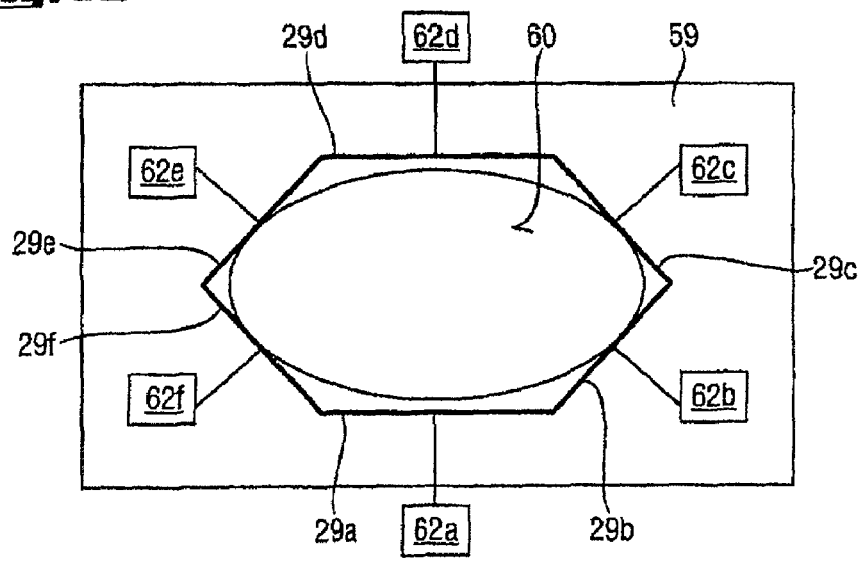
FIG. 16 shows a schematic illustration of a segmented electrode.

One particular electrode arrangement for influencing in a targeted manner, by means of the electromagnetic waves coupled in, the energy distribution of the electrons and/or ions over the surface 60 to be cleaned is illustrated in FIG. 16. In this example, the electrode is composed of six partial electrodes 29a-f, which can each be used as an independent antenna for coupling in electromagnetic waves. Each partial electrode 29a-f can be driven independently by means of the regulator 62a-f respectively, in order to set the frequency and the power of the electromagnetic waves coupled in by the respective partial electrode 29a-f. Different plasma density distributions and different ion/electron energy distributions can be set by means of interferences between the different electromagnetic waves. The choice of six partial electrodes 29a-f in the present example goes back to the elliptical contour of the area 60 to be cleaned, which can be approximated by means of a hexagon. The number of partial electrodes could also be two, three, four, five, seven, eight or more. In order to optimize the cleaning process in the case of inhomogeneously distributed contamination, the electromagnetic waves radiated in can also vary over time, in order to prevent damage to the component 59 to be cleaned particularly when oxidizing plasma gas is used.

Figure 17A:
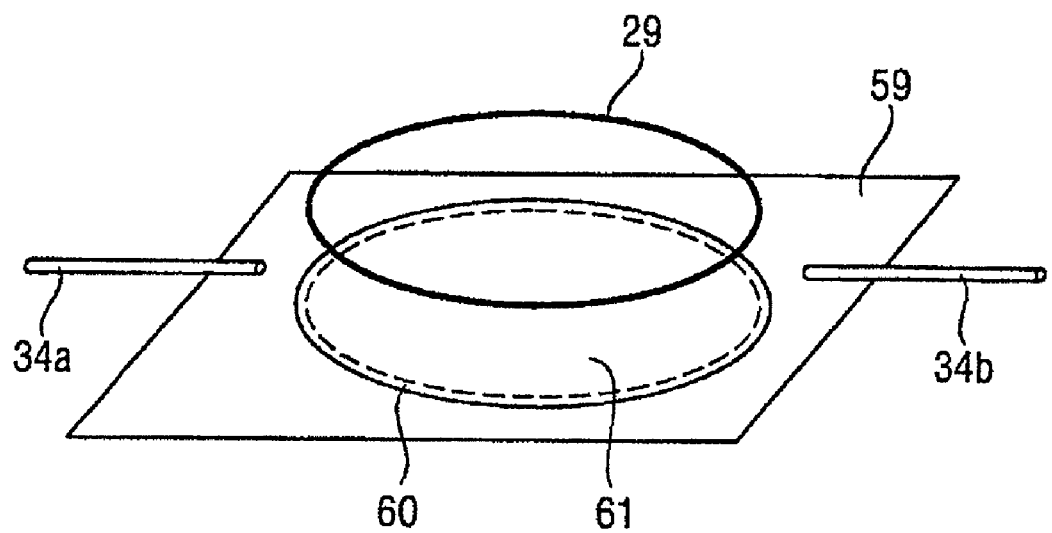
FIG. 17a, b show a schematic illustration of electrode arrangements with a gas feed.
Figure 17B:
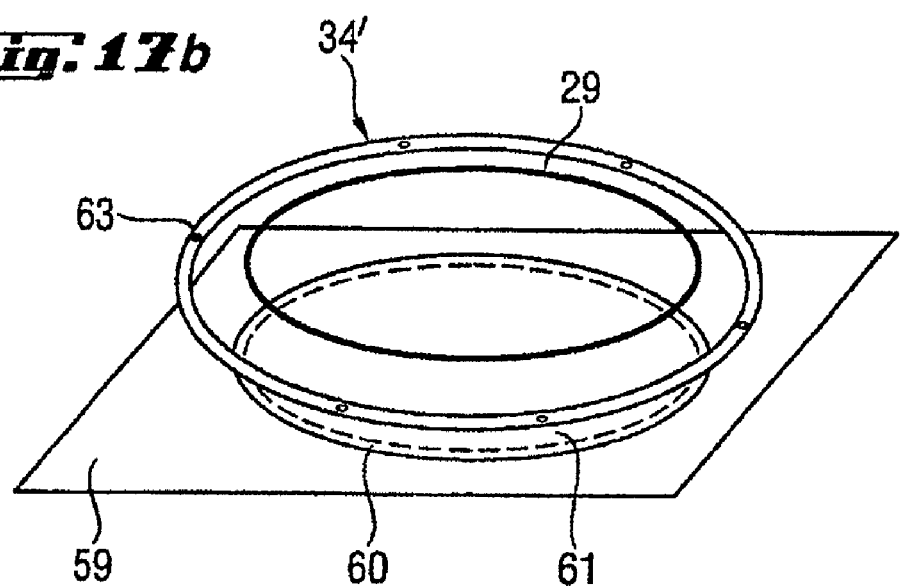
Figure 13:
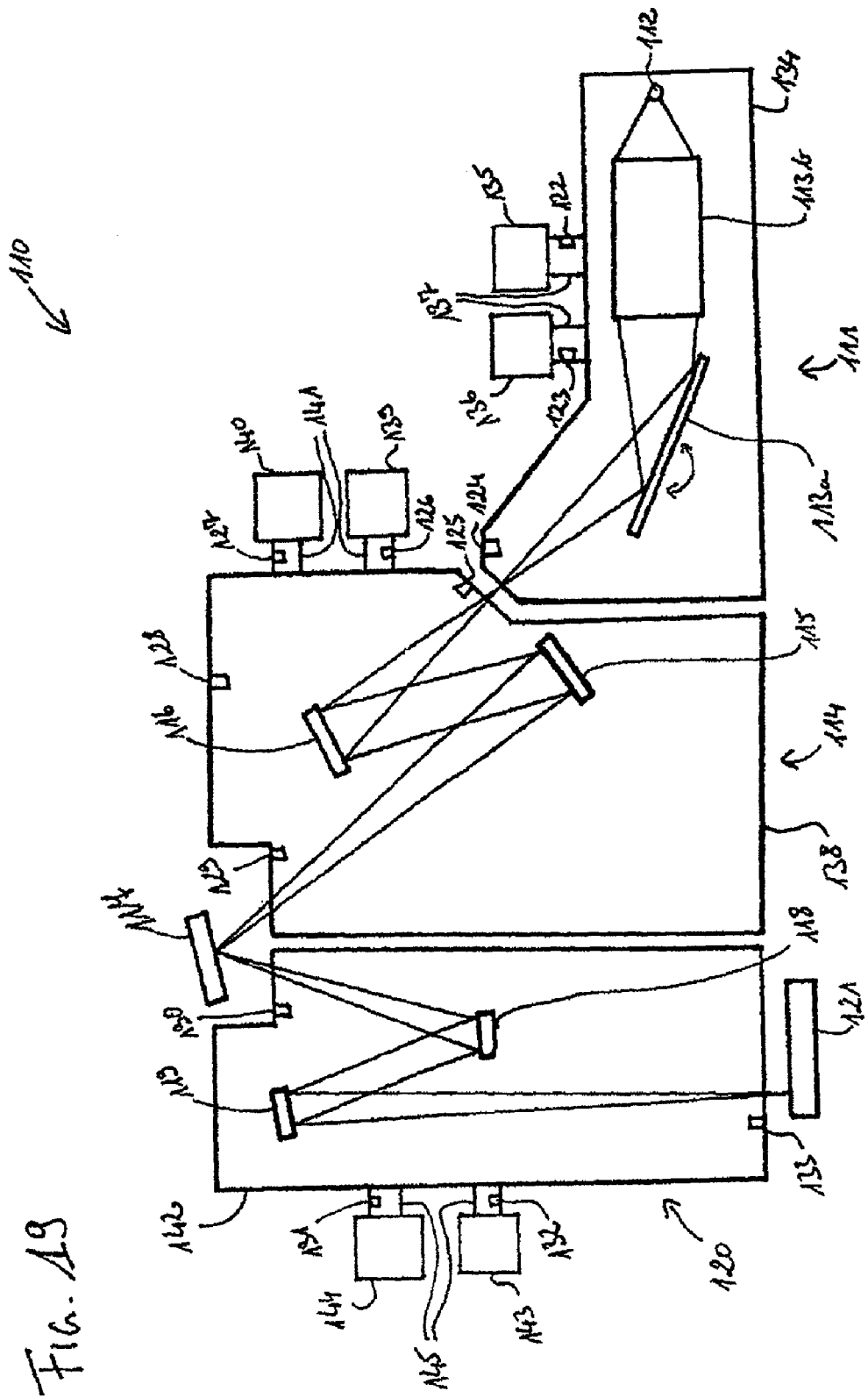

Another approach for generating an inhomogeneous plasma is illustrated in FIGS. 17a,b. For this purpose, in a targeted manner a concentration gradient of the plasma gas or plasma gases is produced in the region in which the plasma is ignited. For this purpose, in FIG. 17a, for example, plasma gas is fed in from opposite sides via the gas feeds 34a,b. In FIG. 17b, a ring-shaped gas feed 34' with openings 63 is used in order to feed in plasma gas from a plurality of sides. A relatively high plasma gas concentration leads to ignition of a plasma even when the electromagnetic wave radiated in has a relatively low power. Here, too, the dashed line indicates the area 61 defined by the electrode 29, said area in this example being somewhat smaller than the area 60 to be cleaned.

Figure 4A:
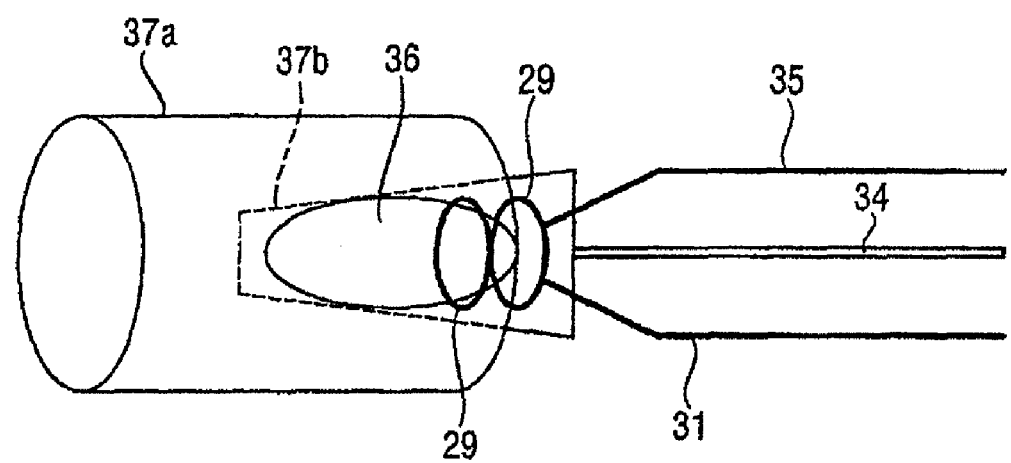
FIGS. 4a, b show schematic two further variant of a plasma and measuring unit, respectively for emission measurements and for transmission measurements.

FIGS. 4a,b schematically show further arrangements of plasma and measuring units which, for their part, are optimized for the measurement of the residual gas atmosphere during the operation of the EUV lithography device or of some other EUV vacuum system. In the present example, an operational environment is taken as a basis in that the partial pressure of the gases that can be used as plasma gas in the residual gas atmosphere does not suffice to ignite a plasma 36 between the electrodes 29. Therefore, a gas feed 34 is also provided alongside the current and voltage supply 35. In order not to appreciably alter the residual gas atmosphere, only the quantity of gas needed to ignite and maintain the plasma 36 is fed in. Therefore, a capillary is preferably used as gas feed 34. The gas flow required can be minimized by choosing the electrode spacing to be as small as possible.

As in the arrangements shown in FIGS. 3a,b too, the plasma 36 is ignited for example by means of high-frequency electromagnetic or microwave radiation. The plasma 36 is situated within an inner shield 37b, which, for its part, is arranged within an outer shield 37a. The inner shield 37b serves principally to catch possibly sputtered electrode material in order that the latter deposits there and does not penetrate into the residual gas atmosphere and lead to contamination. The outer shield serves for locally delimiting the plasma 36. It is preferably embodied in a space-saving manner as a sleeve that is open at its ends in order that the residual gases can advance unimpeded as far as the plasma in order to be detected spectroscopically there. In order to increase the shielding effect, a wide-meshed metallic net comparable to that of the arrangement from FIG. 3b can additionally be provided on at least one of the ends of the outer shield.

Figure 4B:
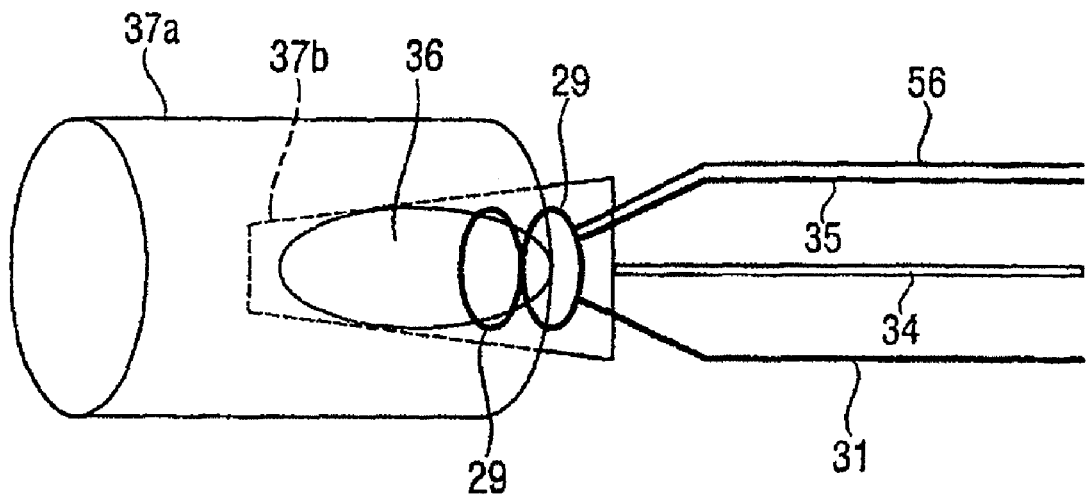

The arrangements from FIG. 4a and FIG. 4b differ with regard to their means for carrying out spectroscopic measurements on the plasma. With the arrangement from FIG. 4a, emission measurements are carried out with the aid of the optical fiber 31. In the arrangement from FIG. 4b, transmission measurement are carried out by means of additionally the optical fiber 56.

In designing the infrastructure for the plasma and measuring unit, but for example also of the optical components such as multilayer mirrors or diaphragms, care should by taken to ensure that their elements such as e.g. drives, data cables, current or voltage cables firstly as far as possible do not exhibit outgassing, in order to keep the risk of contamination low, and secondly are not attacked by the cleaning and/or monitoring plasma, if appropriate. Thus, for example, the PTFE cables usually used are unsuitable since they exhibit outgassing and are attacked by plasmas. With conventional stepper motors, in particular, although high positioning accuracies can be achieved with greased gear mechanisms, they nevertheless lead to high degrees of outgassing.

FIGS. 5a to 8c schematically illustrate some approaches for solutions to these problems.

Figure 5A:
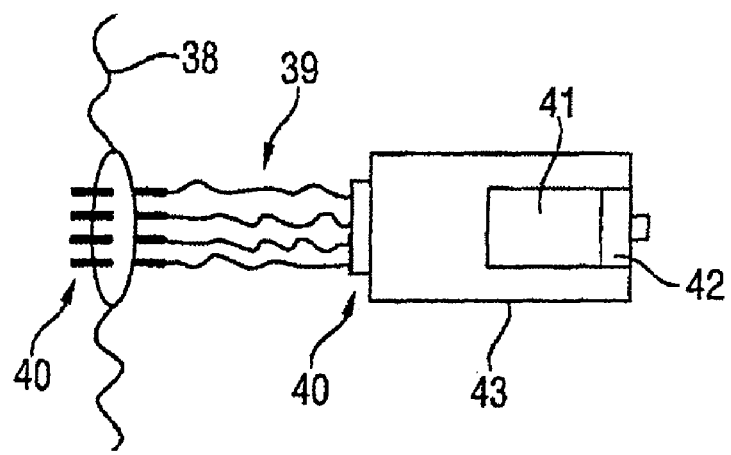
FIGS. 5a, b show schematic a first and second variant of the cabling of a vacuum-suitable drive.

FIG. 5a shows a motor drive 41 comprising stepper motor and gear mechanism on the vacuum side of the wall 38. The unit 41 comprising motor and gear mechanism is encapsulated in the housing 43 in a vacuum tight manner. The electrical feed line is implemented via a vacuum tight bushing 40, e.g. as a vacuum flange with an electrical bushing, in the wall 38 between vacuum and atmosphere and also in the housing 43 in order that no leak to the vacuum arises there either. The best vacuum-tightness is achieved by means of metal seals in this case. The spindle of the motor drive 41 is led into the vacuum via a magnetic coupling 42 in order to transmit the mechanical movement into the vacuum in a manner free of oil and grease. This ensures that the EUV vacuum is not contaminated either during operation or in the event of disturbance of the motor, e.g. as a result of the motor being subjected to overload current. In particular, this enables conventional drives which are not designed for use in a vacuum, but provide very high precision, to be used for the movement of components of the EUV lithography device.

The cables 39 are both data cables for the motor control and electrical lines for the voltage and current supply.

Figure 8A:
FIGS. 8a-c schematically show the construction of vacuum-suitable cables.
Figure 8B:
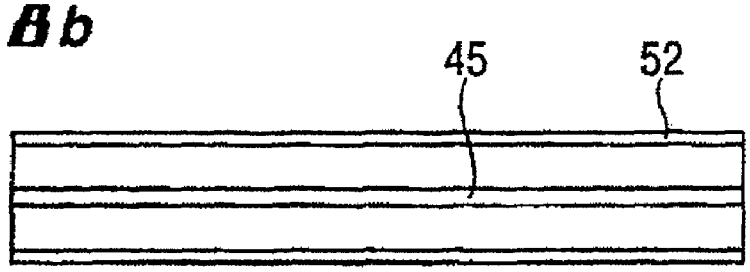

Data cables, whether they are for the motor control or for controlling other units, are preferably sheathed with high-grade steel in order to prevent them from picking up interference signals from the plasma. High-grade steel has the advantage that it exhibits no or only little outgassing and is hardly attacked by plasma. Other suitable sheathing materials include, inter alia, aluminum, aluminum alloys and steels coated in a corrosion-resistant manner. The schematic construction of a cable sheathed with high-grade steel for use as a data cable in the EUV vacuum is illustrated in FIG. 8b, wherein 45 designates the wire serving as the cable and 52 denotes the high-grade steel sheathing. The ends of the data cable should end in vacuum-tight encapsulations that are welded on one side to the outer side of the high-grade steel sheathing and on the other side have a plug equipped with a ceramic plug bushing.

Figure 8C:
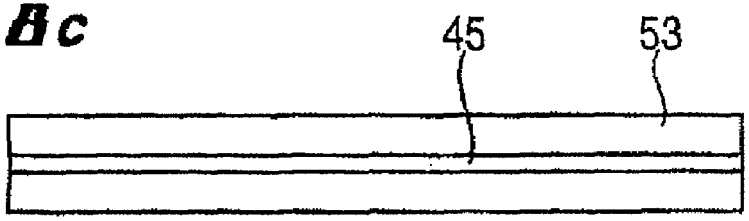

Other lines, via which no signals are communicated, such as the current and voltage supply, for example, do not require a high-grade steel sheathing. They can be embodied e.g. as simple wires 45, e.g. composed of high-grade steel, completely without being enveloped, as illustrated in FIG. 8a, or with a glass sheathing 53, as illustrated in FIG. 8c, as sputtering protection if they have to run very close to a plasma.

Both the data cables and the other cables have to be shaped prior to their actual incorporation and can then be incorporated with the aid of fixings 44, as is shown schematically in FIG. 5b. The fixings 44 are preferably ceramic insulators particularly in the case of wires that are not enveloped or sheathed at all. One example of such a fixing is illustrated in FIG. 6, in which the wire 45 is fixed to a firm support 48 by means of said wire being fixedly clamped in the ceramic component 46 and being fixedly screwed to the firm support 48 by the screw connection 47. With such an arrangement, voltages of up to 2500 V can be transmitted for example in the case of voltage cables.

Since the data and other cables proposed here are rigid and virtually cannot be moved, they are contact-connected by means of moved elements such as, for instance, a motor, preferably as illustrated in FIG. 7. The corresponding cable is connected to a stationary contact plate 49, which, for its part, is contact-connected with spiral wires 50. The spiral wires, in turn, are arranged around the rotary spindle 51 of the drive in the vacuum encapsulation 43, such that a contact-connection is also ensured during operation of the motor when the spindle 51 rotates.

FIG. 10 illustrates, in a flow chart, the sequence of an embodiment of the method for measuring the residual gas atmosphere, in particular for monitoring the residual gas atmosphere within an EUV lithography device. A first step 101 involves defining a limit concentration of a contaminating substance, which corresponds to a specific partial pressure of said substance in the residual gas atmosphere and is manifested for example in an emission spectrum of the plasma as a specific intensity at a wavelength that is characteristic of said substance. In order to start the monitoring of the residual gas atmosphere, in a step 103, a plasma is ignited during normal operation within the EUV lithography device, e.g. within the projection system or the illumination system, the emission spectrum of which plasma is measured (step 105). The present concentration of the contaminating substance is determined from the emission spectrum (step 107). The composition of the residual gas atmosphere can also generally be determined from the spectrum, as required. The present concentration determined is compared with the previously defined limit value in a step 109. If the present concentration lies below the limit value, the EUV lithography device can continue to be operated without a relatively high risk of contamination and steps 105 to 109 can be repeated in the context of further monitoring. Otherwise, operation should be interrupted in order to permit for example an evacuation or a cleaning of the interior of the EUV lithography device (step 111).

FIG. 11 illustrates, in a flow chart, the sequence of an embodiment of the method for cleaning a component of an EUV lithography device. As in the method explained with respect to FIG. 10, a first step 201 involves defining a limit concentration of a contaminating substance, which corresponds to a specific partial pressure of said substance in the residual gas atmosphere and is manifested for example in an emission spectrum of the plasma at a specific intensity at a wavelength that is characteristic of said substance. In order to start the cleaning process, in a step 203, a plasma is ignited directly adjacent to the area of the component that is to be cleaned. In order to monitor the cleaning process in parallel, an emission spectrum of the plasma is recorded (step 205). The present concentration of the contaminating substance is determined from the emission spectrum (step 207). The present concentration determined is compared with the previously defined limit value in a step 209. If the present concentration lies above the limit value, there is still too much contamination present to be able to end the cleaning process, and steps 105 to 109 should be repeated in the context of further monitoring. Otherwise, the cleaning process can be ended (step 211). This very near-instantaneous monitoring of the cleaning process can prevent the situation where the component to be cleaned is exposed to the cleaning plasma for too long and is thereby possibly irreversibly damaged, which can easily happen particularly in the case of optical components based on multilayer systems.

It should be pointed out that the concentration of more than just one contaminating substance can also be monitored simultaneously. Depending on what is required, measurements can be carried out continuously or measurements can be carried out in the manner of random sampling at relatively long time intervals. The first possibility is appropriate particularly when monitoring a cleaning process, and the second possibility when monitoring the residual gas atmosphere during ongoing operation of an EUV lithography device.

The methods described here can moreover also be carried out using transmission spectroscopy.

It should furthermore be pointed out that both the monitoring of the cleaning process and the monitoring of the residual gas atmosphere can be automated by connecting the plasma and measuring units to a supervision and control device, which, if appropriate, also performs the evaluation of the spectroscopic measurement. Moreover, it is advantageous for, in particular, the continuous operation of the EUV lithography device to design the supervision and control unit in such a way that, for example, the cleaning process is automatically begun and ended and the operation of the EUV lithography device is automatically interrupted.

FIG. 19 schematically illustrates an EUV lithography device 110. Essential components are the beam shaping system 111, the illumination system 114, the photomask 117 and the projection system 120. The EUV lithography device 110 is operated under vacuum conditions in order that the EUV radiation is absorbed as little as possible in its interior.

By way of example, a plasma source or else a synchrotron can serve as radiation source 112. The emerging radiation in the wavelength range of approximately 5 nm to 20 nm is firstly concentrated in the collimator 113*b*. Moreover, the desired operating wavelength is filtered out with the aid of a monochromator 113*a* by varying the angle of incidence. In the stated wavelength range, the collimator 113*b* and the monochromator 113*a* are usually embodied as reflective optical elements. Collimators are often reflective optical elements embodied in shell-shaped fashion in order to achieve a focusing or collimating effect. The reflection of the radiation takes place at the concave area, in which case often a multilayer system is not used on the concave area for reflection purposes, since a widest possible wavelength range is intended to be reflected. The filtering out of a narrow wavelength band by reflection takes place at the monochromator, often with the aid of a grating structure of a multilayer system.

The operating beam conditioned with regard to wavelength and spatial distribution in the beam shaping system 111 is then introduced into the illumination system 114. In the example illustrated in FIG. 19, the illumination system 114 has two mirrors 115, 116. The mirrors 115, 116 direct the beam onto the photomask 117, which has the structure that is intended to be imaged onto the wafer 121. The photomask 117 is likewise a reflective optical element for the EUV and soft wavelength range, which is exchanged depending on the production process. With the aid of the projection system 120, the beam reflected from the photomask 117 is projected onto the wafer 121 and the structure of the photomask is thereby imaged onto said wafer. In the example illustrated, the projection system 120 has two mirrors 118, 119. It should be pointed out that the projection system 120 and the illumination system 114 can in each case have just one or else three, four, five or more mirrors.

In the example illustrated in FIG. 19, the vacuum system of the EUV lithography device 110 is subdivided into different vacuum subsystems each having a dedicated vacuum chamber and a backing pump and a main pump. FIG. 19 illustrates, as vacuum systems configured independently of one another at least to an extent such that the vacuum can be adapted to the possibly different conditions in different components, the vacuum system of the beam shaping system 111 comprising vacuum chamber 134, backing pump 135 and main pump 136, of the illumination system 114 comprising vacuum chamber 138, backing pump 139 and main pump 140, and of the projection system 120 comprising vacuum chamber 142, backing pump 143 and main pump 144. In order to ensure a high vacuum, in the present example not just one pump per vacuum system is employed, but rather in each case a backing pump 135, 129, 143, which initially provide a vacuum which is of relatively low quality but which suffices to turn on the respective main pump 136, 140, 144, which, for its part, provides the vacuum required for the operation of the EUV lithography device. Depending on the requirements, a vacuum system can also have a combination of three, four, five or more pumps. The pumps can be directly connected to the vacuum chambers; in the example illustrated in FIG. 19, the pumps are connected to the respective vacuum chambers via feed lines 137, 141, 145. The subdivision with regard to the vacuum can permit a faster evacuation of the EUV lithography device at the beginning of starting operation.

In the exemplary embodiment described here, the gas discharge is initiated in the form of a spark discharge. A spark can be ignited well using simple technical means and in a locally highly delimited space and leads to a momentary gas discharge. Between two electrodes, for example, a strong electric field or a high voltage is applied, which leads to an excitation of the electrons of the matter present in the gas phase between the electrodes, which for its part, leads to the emission of photons upon the de-excitation of the electrons. The emitted photons are perceived as a spark and are detected, preferably measured spectroscopically, in order to obtain information about the presence of contaminating materials.

Symbolically illustrated modules 122-133 are arranged at different locations within the EUV lithography device 110, said modules having means for igniting a spark and means for spectroscopically measuring the radiation emitted by the spark. It should be pointed out that the means for igniting a spark and the means for spectroscopically measuring the radiation emitted by the spark can likewise be arranged as such within the EUV lithography device 110. In this case, in particular, the means for igniting a spark can be introduced into the vacuum to be monitored for example via electrical bushings in the feed lines or vacuum chamber walls.

The module 128 is arranged in such a way that generally the contamination within the illumination system 114 can be measured. The modules 124, 125, 129, 130 and 133 are arranged in the vicinity of vacuum locks in respect of poorer vacuum conditions, in order to detect possible weak points in the locks and therefore increased contamination during the operation of the EUV lithography device. The module 133 is particularly important in this case since the wafer 121 for the exposure process can be coated with photoresist, which can exhibit outgassing and can lead to highly damaging contamination of the mirrors 118, 119 upon ingress into the vacuum chamber 142 of the projection system 120.

Moreover, modules 122, 123, 126, 127, 131, 132 are arranged in the feed lines 137, 141, 145 from the pumps 135, 136, 139, 140, 143, 144 to the vacuum chambers 134, 138, 142. This is because pumps can also be a serious source of contamination. Although pumps do not exhibit outgassing when operated correctly or are free of lubricant on the vacuum side, their gear mechanisms are often lubricated with fluorocarbons such as e.g. fluorinated polyethers or alternatively, in the case of the pumps used as backing pumps, with oil or grease. Although the lubricants have a low vapor pressure, too much thereof can nevertheless outgas in vacuum sufficient for EUV lithography operation. The outlay for removing the contamination caused by such lubricants is very high: the EUV lithography device 110 would have to be heated at temperatures significantly above 100° C. for several days, which can lead to irreparable damage to the mirrors 115, 116, 118, 119. It is therefore of great importance for smooth operation under good conditions that leaks and damage on the pumps are detected as rapidly as possible and appropriate reactions thereto can be effected, for example by increasing the capacity of the remaining pumps, feeding in other substances that react with the lubricant outgassings to form harmless volatile substances, or even completely interrupting operation. It is advantageous in this connection that in particular in the feed lines to the backing pumps 135, 139, 143, in which the vacuum, under certain circumstances, is not quite as high as in the respective vacuum chamber 134, 138, 142, a spark can be ignited particularly easily. A sudden high degree of outgassing on account of pump damage can also be detected as increased contamination in the gas phase, since sparks can also be ignited at atmospheric pressure. In contrast to the spark emission measurement presented here, conventional residual gas analyzers cannot be used for such cases, since they can generally only be used at pressures of $10^{-5}$ mbar or lower and then also have a low detection sensitivity.

Two preferred embodiments of a module 146 comprising means 149, 153 for igniting a spark 150 and means 151, 152 for spectroscopically measuring the radiation 150 emitted by the spark for incorporation into an EUV lithography device are schematically illustrated in FIGS. 20*a,b*. The examples illustrated in FIGS. 20*a,b* are optimized for incorporation into pump feed lines by virtue of the fact that the module 146 is embodied as a pipe section having a flange 147 for connection to the feed line 148 at both ends. It is also possible for the pump and/or the backing chamber to be directly connected to the two flanges. It is likewise possible for the module to be embodied for example as open at only one side and provided with a flange in order to connect it to a vacuum chamber wall or feed line, for instance.

Independently of the outer configuration of the module, the means for igniting a spark 150 can be embodied for example as an electrode pair 149, as illustrated in FIG. 20a. In one modification, the module wall or a wall of the vacuum chamber, of the feed line or of the pump can also serve as a counter electrode, such that only one of the two electrodes 149 is sufficient. Given a correspondingly small spacing with respect to the counter electrode, the electrodes can be designed to be very small and in a space-saving manner, such that no impairment of operation of the EUV lithography device is to be expected as a result of the spark 150.

The use of a spark plug 153 for igniting a spark 150, as illustrated in FIG. 20b, is particularly preferred. Spark plugs are cost-effective and readily available. Since they are generally composed of ceramic and therefore, even upon irradiation with EUV or soft X-ray radiation, do not outgas and contribute to the contamination in the gas phase, they are well suited to use in the vacuum in EUV lithography devices.

A combination of optical fiber 151 projecting into a vacuum and spectroscope 152 arranged outside the EUV vacuum is preferably used for carrying out the spectroscopic measurement of the radiation emitted by the spark. Optical fibers, in particular glass fibers, also have the advantage that they do not outgas in the vacuum even upon irradiation with EUV or soft X-ray radiation and, moreover, have a minimal space requirement, such that operation of the EUV lithography device is not impaired. All remaining components which would be necessary for the measurement but have a certain space requirement and, if appropriate, are not vacuum-suitable are combined in the spectrometer 152 situated externally in the present example.

One example of a suitable embodiment of the spectrometer 152 is illustrated schematically in FIG. 21. For coupling the emitted photons into the optical fiber 151, a coupling-in unit 154 is provided at one end of said fiber. For coupling out the photons from the optical fiber 151, a corresponding coupling-out unit 155 is provided at the other end of said fiber. From there the photons enter into an energy-dispersive analyzer, for example a grating monochromator 156, in order to record an energy-resolved spectrum of the emitted photons. For this purpose, the photons are diffracted by a different angle at the grating monochromator 156 depending on their energy or wavelength, such that they impinge at different locations on a two-dimensional detector, here a CCD detector 157. Upon impinging on the detector 157, the photons are converted into electric current which is proportional to the number of photons in the respective energy range and is read out separately for each energy range. In the present example, a transient recorder 159 is used for this purpose. A transient recorder is understood to mean a fast data memory that can pick up and store a large quantity of data in a short time, such that it can for example run through many emission spectra per second over a characteristic energy range and digitize them. In the present example, the transient recorder 159 is clocked so rapidly that it can completely read from the CCD detector 157 via the read-out cable 158 more than once during the lifetime of a spark. Additional information about the present contamination can thereby be obtained, as will be explained below. It should be pointed out that it is also possible to use devices for reading from the detector which read from the detector just once per spark, since the essential information about the contamination can be obtained thereby. By way of example, conventional oscilloscopes are suitable for this purpose. In the simplest case, it is also possible to dispense with the energy resolution by the protons being measured directly or with the aid of an optical fiber by a photodetector. Fluctuations in the amount of contaminating substances in the gas phase are then manifested in a fluctuation in the photocurrent generated.

Figure 22A:
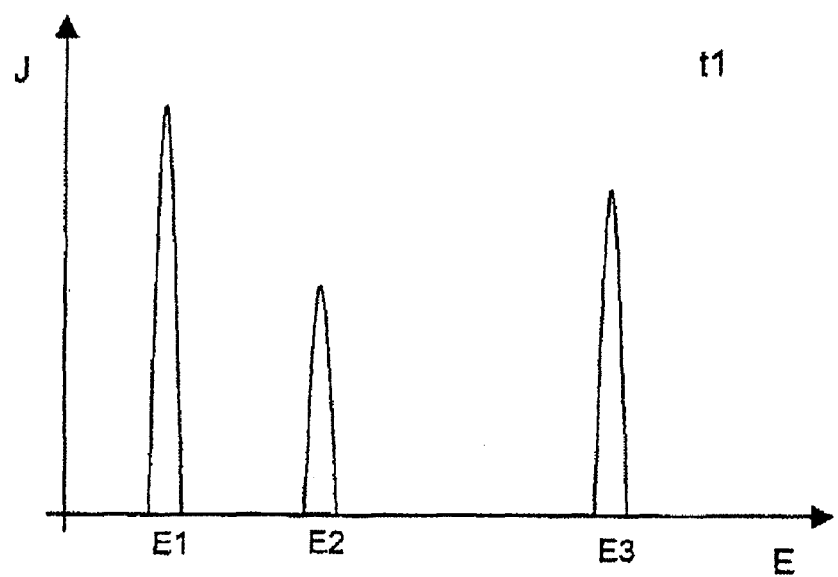
FIGS. 22a, b show schematic emission spectra at different instants t1, t2 of the spark lifetime.
Figure 22B:
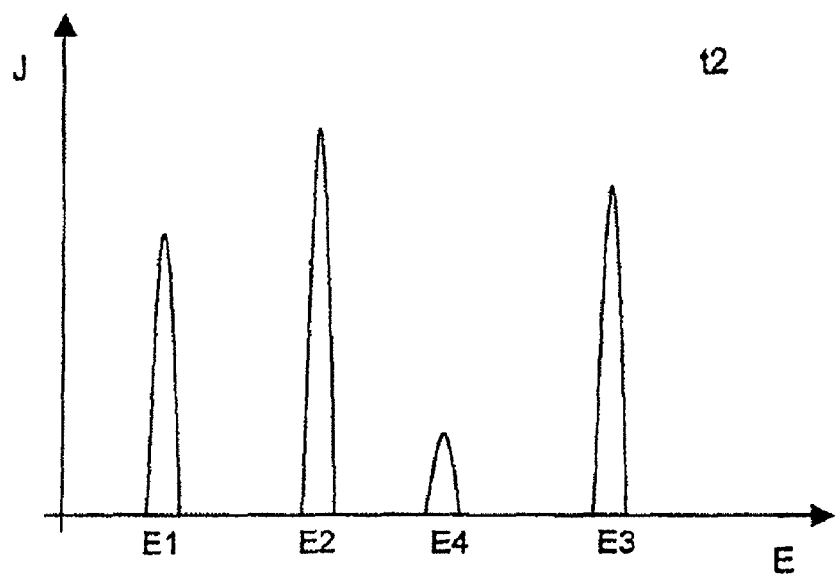

FIGS. 22a,b schematically illustrate two spectra in the case of energy-resolved measurement of the photons emitted by the spark. For this purpose, in arbitrary units, the measured current J, which is equivalent to the photon intensity or number of photons and thus to the amount of specific contaminating substances, is plotted against the energy E. In this case, the spectra were recorded at different instants t1 and t2 during the lifetime of a spark. Since the energy E of the emitted photons are dependent on the respective quantum-mechanical energy levels within the atoms and molecules excited during the spark discharge, the energies or the energy combinations of the emitted photons are characteristic of the respective atoms or molecules. In the spectrum shown in FIG. 22a, at the beginning of the spark lifetime, photons can be detected in different numbers at three different energies E1, E2, E3, which correspond to three different substances in different concentrations for the sake of simpler illustration here. Since the spectrum was recorded at the beginning of the spark lifetime, it can be assumed that contamination from the gas phase is substantially involved. By contrast, the spectrum shown in FIG. 4b was recorded at the end of the spark lifetime. In comparison with instant t1, more photons having the energy E2 and additionally photons having the energy E4 are present. This can be interpreted such that this represents not only the contamination in the gas phase but also the surface contamination on the electrodes, which undergoes transition to the gas phase at least in part as a result of the spark discharge. The photons having the energy E4 are an indication of a contamination which is not volatile without spark action and which has already deposited on surfaces within the vacuum system. The photons having the energy E2 are an indication of a substance which is present both in the gas phase and in nonvolatile fashion on the surface. The photon intensity at E3 remains unchanged, which indicates a substance only in the gas phase. The photon intensity at E1 decreases over the lifetime of the spark, which can happen if a substance is not only excited but also decomposed by the spark. In the case of specific substances, temporal alterations in the photon intensity over the lifetime of the spark are also caused by fluorescence effects which involve the photons being emitted spontaneously only with a delay. Through careful evaluation of the spectra at different instants in the lifetime of the spark, it is therefore possible to make extremely precisely about the contaminating substances currently present in the vacuum system and their state.

If the state of the contaminating substances in the gas phase or on the surface is not of importance, one spectroscopic measurement per spark is sufficient. Through comparison with the previously measured spectra, it is possible to detect alterations in the concentration and, if appropriate, composition in the case of a plurality of substances of the contamination. For monitoring the contamination during the operation of an EUV lithography device it may suffice to observe only the fluctuation of the total concentration of the contaminating substances, e.g. if other monitoring methods are additionally used as well, or if the intention is only to monitor for pump damage or leaks which would be manifested in a sudden and noticeable increase in total concentration. In such cases, it is also possible to dispense with the energy resolution during the photon measurement and, by way of example, a simple photon detector or a camera is sufficient for detecting the occurrence of emitted radiation.

Figure 23:
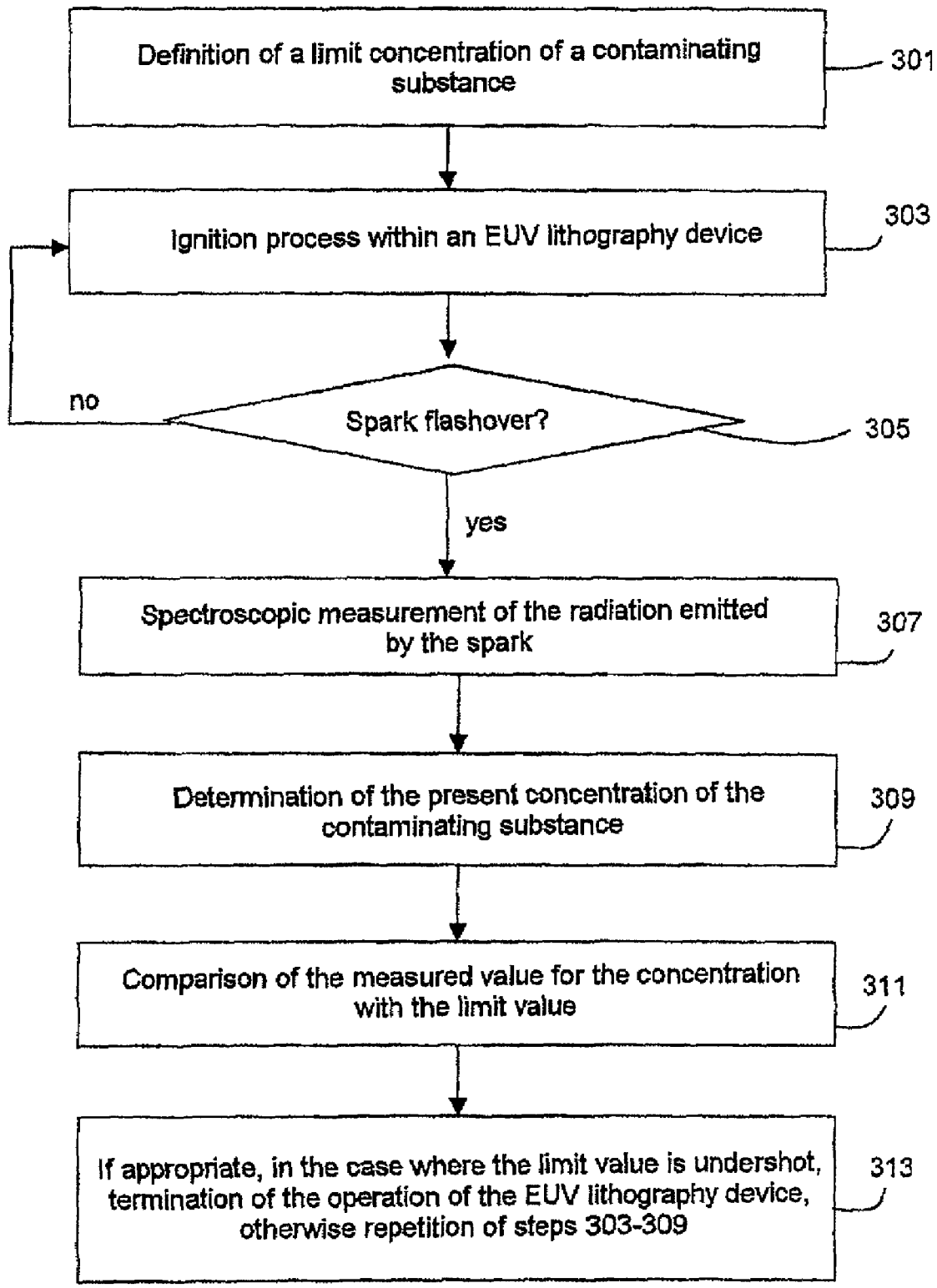
FIG. 23 shows a flow chart concerning an embodiment of the method for measuring the contamination.

FIG. 23 illustrates, in a flow chart, one example for carrying out the contamination measurement method proposed here. In a first step 301, firstly a limit concentration of a contaminating substance which is intended in particular to be monitored is defined. Which contaminating substances should expediently be monitored and where the respective limit concentrations lie depend on the concrete EUV lithography device and its components and on the operating conditions. In a further step 303, an attempt is made to ignite a spark between the electrodes arranged within an EUV lithography device. This is only possible, however, if the pressure within the EUV lithography device exceeds a certain minimum value, that is to say more matter is present in the gas phase. By setting the electrode spacing and the ignition voltage, it is possible to achieve the effect that a spark flashes over starting from a specific vacuum deterioration. The latter is preferably chosen such that contamination of the optical elements, in particular of the mirrors, to a significant extent is not yet to be expected. As long as a spark does not yet flash over, the ignition process is repeated from time to time (step 305). As soon as a spark flashes over, the spectroscopic measurement of the radiation emitted by the spark is carried out (step 307). The signal that a spark has flashed over can be utilized, as required, for example to report this information to a central controller and, if appropriate, to increase the pump capacity or to implement other measures. The present concentration of the respective substance can be determined from the spectroscopic measurement (step 309) and be compared with the limit value (step 311). Should the limit value be exceeded, the EUV lithography operation should be ended before for example the mirrors or other components are damaged, or some other suitable measure should be implemented. Otherwise, the abovementioned steps can be repeated (step 313) in order to continue to monitor the contamination in the gas phase continuously during the operation of the EUV lithography device. In more complex embodiments, it is likewise possible to monitor the size of the spark in order to draw additional conclusions therefrom about an impairment or improvement of the vacuum.

It should be pointed out that although a gas discharge in the form of a spark discharge is described in the context of this exemplary embodiment, other types of gas discharge can also be used, such as, for instance, corona discharge or arc discharge, inter alia. For detecting the emitted radiation, too, other known means can also be used in addition to the means illustrated here. Like the choice of how a gas discharge is intended to be initiated, the manner of detecting the radiation is at the discretion of the person skilled in the art, who will implement the suitable measures according to the boundary conditions of the measurement environment and the type of measurement results desired.

Furthermore, it should be pointed out that for the measurement of the residual gas atmosphere it is possible to have recourse to a module comprising means for initiating a gas discharge, and also for measuring the contamination it is possible to have recourse to a module comprising means for igniting a plasma. In both measurements a spectroscopic analysis is carried out, which can be evaluated according to the respective issue. In particular, it is also possible to provide modules which have both means for initiating a gas discharge and means for igniting a plasma, wherein, depending on the desired measurement, a gas discharge is initiated or a plasma is ignited and spectroscopically analyzed and evaluated.

The invention claimed is:

1. A method for measuring the residual gas atmosphere within the interior of a vacuum chamber of an illumination system or a projection system of an EUV lithography device for the extreme ultraviolet and soft X-ray wavelength range, comprising igniting a plasma in the interior of the vacuum chamber during the operation of the EUV lithography device, and performing a spectroscopic measurement on the plasma.

2. A device comprising a module for measuring the residual gas atmosphere within an interior of a vacuum chamber of an illumination system or a projection system of an EUV lithography device for the extreme ultraviolet and soft X-ray wavelength range, the module comprising an arrangement for igniting a plasma and an apparatus for measuring the emission or transmission of the plasma arranged within a shield.

3. A device comprising a module for igniting a plasma arranged within a vacuum chamber of an illumination system or a projection system of an EUV lithography device for the extreme ultraviolet and soft X-ray wavelength range, the module comprising, in an interior of the module, an electrode for igniting the plasma, wherein the electrode is sheathed with a sputter-resistant material, wherein the electrode is arranged adjacent to a delimited surface and wherein a form of the electrode is adapted to the contour of the surface such that an ignited plasma propagates over a region whose extent is restricted with a maximum deviation of approximately ±20% to the delimited surface.

4. A method for measuring contamination within an interior of a vacuum chamber of an illumination system or a projection system of an EUV lithography device for the extreme ultraviolet and soft X-ray wavelength range, comprising, within the vacuum system, utilizing a spark discharge to excite electrons from matter present in the gas phase to a higher energy level, and detecting the radiation which the exited electrons emit in the transition from the higher energy level to a lower energy level.

5. A device comprising a module for measuring the contamination within an interior of a vacuum chamber of an illumination system or a projection system of an EUV lithography device for the extreme ultraviolet and soft X-ray wavelength range, comprising, in the interior of the vacuum chamber, a spark plug for initiating a gas discharge and a detector for detecting the contamination within the vacuum system from the radiation emitted as a result of the gas discharge.

6. The method as claimed in claim 1, wherein the plasma is ignited by a gas already present in the interior of the vacuum chamber and is locally delimited, and wherein the spectroscopic measurement is carried out continuously.

7. The method as claimed in claim 1, wherein, for a contaminating substance, a limit value for the partial pressure thereof in the residual gas atmosphere is defined, above which limit value the operation of the vacuum system is terminated, and further comprising comparing the value determined spectroscopically with the limit value.

8. The device as claimed in claim 2, wherein the apparatus detects radiation emitted on account of the gas discharge and comprises an energy-dispersive analyzer and a two-dimensional detector.

9. The device as claimed in claim 2, further comprising, in its interior, a detector for carrying out spectroscopic measurements.

10. The device as claimed in claim 3, further comprising, in its interior, a detector for carrying out spectroscopic measurements.

11. The device as claimed in claim 5, further comprising, in its interior, a detector for carrying out spectroscopic measurements.

12. The device as claimed in claim 2, wherein the module comprises an optical fiber for measuring the emission or transmission of the plasma, and wherein a spectroscope arranged outside the vacuum system is connected to the optical fiber.

13. The device as claimed in claim 3, wherein the module comprises an optical fiber for measuring the emission or transmission of the plasma, and wherein a spectroscope arranged outside the vacuum system is connected to the optical fiber.

14. The device as claimed in claim 5, wherein the module comprises an optical fiber for measuring the radiation emitted as a result of the gas discharge, and wherein a spectroscope arranged outside the vacuum system is connected to the optical fiber.

15. The device as claimed in claim 2, further comprising a gas feed, which opens at the location at which the plasma is ignited.

16. The device as claimed in claim 3, further comprising a gas feed, which opens at the location at which the plasma is ignited.

17. The device as claimed in claim 5, further comprising a gas feed, which opens at the location at which the gas discharge is ignited.

18. The device as claimed in claim 2, further comprising motor-gear units encapsulated in a vacuum-tight manner in order to move moveable components.

19. The device as claimed in claim 3, further comprising motor-gear units encapsulated in a vacuum-tight manner in order to move moveable components.

20. The device as claimed in claim 5, further comprising motor-gear units encapsulated in a vacuum-tight manner in order to move moveable components.

21. The device as claimed in claim 2, further comprising wires or glass-enveloped wires for supplying at least one of current and voltage to components in the interior.

22. The device as claimed in claim 3, further comprising wires or glass-enveloped wires for supplying at least one of current and voltage to components in the interior.

23. The device as claimed in claim 5, further comprising wires or glass-enveloped wires for supplying at least one of current and voltage to components in the interior.

24. The device as claimed in claim 3, wherein the electrode defines an area which covers the delimited surface to a degree of 70-150%, whereby the delimited surface is an area to be optically utilized of a reflective optical element.

25. The device as claimed in claim 3, wherein the electrode is embodied such that a density distribution of the plasma is set such that a higher removal is effected in surface regions of the delimited surface having a higher degree of contamination than in surface regions having a lower degree of contamination.

26. The device as claimed in claim 3, further comprising an arrangement, to couple in electromagnetic waves in the frequency range of between $10^3$ Hz and $10^{11}$ Hz, having adjustable power.

27. The device as claimed in claim 3, wherein the electrode is sheathed with a fused silica and is arranged in a shield.

28. The method as claimed in claim 4, wherein the emitted radiation is measured in an energy-resolved or time-resolved manner.

29. The device as claimed in claim 5, further comprising a feed line between the vacuum chamber and a pump, wherein the spark plug for initiating a gas discharge and the detector for detecting the contamination within the vacuum system from the radiation emitted as a result of the gas discharge is arranged in the feed line.

30. The device as claimed in claim 5, wherein the detector for detecting the contamination within the vacuum system from the radiation emitted as a result of the gas discharge has a transient recorder.

* * * * *

UNITED STATES PATENT AND TRADEMARK OFFICE
CERTIFICATE OF CORRECTION

PATENT NO.        : 7,911,598 B2
APPLICATION NO.   : 12/555620
DATED             : March 22, 2011
INVENTOR(S)       : Dieter Kraus et al.

It is certified that error appears in the above-identified patent and that said Letters Patent is hereby corrected as shown below:

Column 5, Line 11: delete "FIG." and insert --FIGS.--

Column 14, Line 38: delete "by" and insert --be--

Signed and Sealed this
Third Day of July, 2012

David J. Kappos
*Director of the United States Patent and Trademark Office*